US010231866B1

(12) United States Patent
Kammer et al.

(10) Patent No.: US 10,231,866 B1
(45) Date of Patent: Mar. 19, 2019

(54) PRODUCING STERILE SURGICAL SLUSH USING COMPLEX ROTATIONAL MOTION

(71) Applicant: C Change Surgical LLC, Winston-Salem, NC (US)

(72) Inventors: Patrick Kammer, Greensboro, NC (US); Kevin Joseph Rackers, Summerfield, NC (US); Benjamin A. Perrot, Greensboro, NC (US)

(73) Assignee: C Change Surgical LLC, Winston-Salem, NC (US)

( * ) Notice: Subject to any disclaimer, the term of this patent is extended or adjusted under 35 U.S.C. 154(b) by 99 days.

(21) Appl. No.: 15/602,964

(22) Filed: May 23, 2017

Related U.S. Application Data

(63) Continuation of application No. 14/064,972, filed on Oct. 28, 2013, now Pat. No. 9,693,892, which is a continuation of application No. 12/965,670, filed on Dec. 10, 2010, now abandoned, which is a continuation-in-part of application No. 12/477,635, filed on Jun. 3, 2009, now Pat. No. 7,874,167.

(60) Provisional application No. 61/059,732, filed on Jun. 6, 2008.

(51) Int. Cl.
*A61F 7/12* (2006.01)
*A61F 7/00* (2006.01)
*B01F 3/22* (2006.01)
*B01F 11/00* (2006.01)

(52) U.S. Cl.
CPC ............. *A61F 7/12* (2013.01); *A61F 7/0085* (2013.01); *B01F 3/2269* (2013.01); *B01F 11/0002* (2013.01); *F25C 2301/002* (2013.01)

(58) Field of Classification Search
CPC ........ A61F 7/0085; A61F 7/12; B01F 9/0001; B01F 11/0002; B01F 11/0062; B01F 3/2215; B01F 3/2269; F25C 2301/002
See application file for complete search history.

(56) References Cited

U.S. PATENT DOCUMENTS

| | | |
|---|---|---|
| 71,448 A | 11/1867 | Bruckner |
| 714,415 A | 11/1902 | Trafford |
| 2,555,624 A | 6/1951 | Anderson et al. |
| 2,993,350 A | 7/1961 | Smith et al. |
| 3,998,070 A | 12/1976 | Mueller |
| 4,393,659 A | 7/1983 | Keyes et al. |
| 4,435,082 A | 3/1984 | Bishop |
| 4,526,012 A | 7/1985 | Chigira |
| 4,580,405 A | 4/1986 | Cretzmeyer, III |
| 4,669,274 A | 6/1987 | Huang |
| 4,722,198 A | 2/1988 | Huang |
| 4,813,243 A | 3/1989 | Woods et al. |
| 4,934,152 A | 6/1990 | Templeton |

(Continued)

FOREIGN PATENT DOCUMENTS

JP 06123532 5/1994

*Primary Examiner* — Timothy C Cleveland
(74) *Attorney, Agent, or Firm* — Kevin E Flynn; Flynn IP Law

(57) ABSTRACT

Methods and apparatus for producing saline slush for surgical applications. A mixture comprising water and salt within a receptacle is attached to an assembly for making surgical slush while imposing complex rotational motion upon the receptacle. The complex rotational motion including rotating the platform with the attached receptacle around a first axis that runs through the platform while rotating the platform around an orbital axis different from the first axis to impose a complex motion upon the fluid within the receptacle.

6 Claims, 39 Drawing Sheets

(56) References Cited

U.S. PATENT DOCUMENTS

| | | |
|---|---|---|
| 5,163,299 A | 11/1992 | Faries, Jr. et al. |
| 5,174,306 A | 12/1992 | Marshall |
| 5,282,368 A | 2/1994 | Ordoukhanian |
| 5,331,820 A | 7/1994 | Faries, Jr. et al. |
| 5,333,326 A | 8/1994 | Faries, Jr. et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,457,962 A | 10/1995 | Faries, Jr. et al. |
| 5,502,980 A | 4/1996 | Faries, Jr. et al. |
| 5,522,095 A | 6/1996 | Faries, Jr. et al. |
| 5,524,643 A | 6/1996 | Faries, Jr. et al. |
| 5,551,240 A | 9/1996 | Faries, Jr. et al. |
| 5,615,423 A | 4/1997 | Faries, Jr. et al. |
| 5,653,938 A | 8/1997 | Faries, Jr. et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,950,438 A | 9/1999 | Faries, Jr. et al. |
| 6,003,328 A | 12/1999 | Faries, Jr. et al. |
| 6,035,855 A | 3/2000 | Faries, Jr. et al. |
| 6,087,636 A | 7/2000 | Faries, Jr. et al. |
| 6,091,058 A | 7/2000 | Faries, Jr. et al. |
| 6,148,634 A | 11/2000 | Sherwood |
| 6,255,627 B1 | 7/2001 | Faries, Jr. et al. |
| 6,371,121 B1 | 4/2002 | Faries, Jr. et al. |
| 6,802,802 B2 | 10/2004 | Woog |
| 6,810,881 B2 | 11/2004 | Faries, Jr. et al. |
| 6,860,271 B2 | 3/2005 | Faries, Jr. et al. |
| 6,910,485 B2 | 6/2005 | Faries, Jr. et al. |
| 6,910,801 B2 | 6/2005 | Sasaki |
| 6,918,395 B2 | 7/2005 | Faries, Jr. et al. |
| 7,176,030 B2 | 2/2007 | Faries, Jr. et al. |
| 7,269,970 B2 | 9/2007 | Robertson |
| 7,347,210 B2 | 3/2008 | Faries, Jr. et al. |
| 7,350,373 B1 | 4/2008 | Faries, Jr. et al. |
| 7,389,653 B2 | 6/2008 | Kasza et al. |
| 7,418,966 B2 | 9/2008 | Faries, Jr. et al. |
| 7,419,070 B2 | 9/2008 | Cantwell et al. |
| 7,874,167 B2 | 1/2011 | Kammer et al. |
| 8,057,092 B2 | 11/2011 | Ryan et al. |
| 8,148,666 B2 | 4/2012 | Faries, Jr. et al. |
| 8,348,186 B2 | 1/2013 | Seidler et al. |
| 2005/0247169 A1 | 11/2005 | Faries et al. |
| 2006/0194324 A1 | 8/2006 | Faries et al. |
| 2006/0260443 A1 | 11/2006 | Faries et al. |
| 2008/0017292 A1 | 1/2008 | Gammons et al. |
| 2010/0293965 A1 | 11/2010 | Frank |

PRODUCING STERILE SURGICAL SLUSH USING COMPLEX ROTATIONAL MOTION

This application claims priority to and incorporates by reference co-pending U.S. patent application Ser. No. 14/064,972 for Method of Producing Slush for Surgical Use Through Receptacle Oscillation filed Oct. 28, 2013. The '972 application claimed priority to and incorporated by reference then co-pending U.S. patent application Ser. No. 12/965,670 for Devices for Producing Sterile Therapeutic Medium filed Dec. 10, 2010. The '670 application claimed priority to then co-pending U.S. patent application Ser. No. 12/477,635 for Method and Apparatus for Producing Slush for Surgical Use filed Jun. 3, 2009, subsequently issued as U.S. Pat. No. 7,874,167 issued on Jan. 25, 2011. Through the chain of priority claims including the '635 application, this application claims the benefit of and incorporates by reference U.S. Provisional Application No. 61/059,732 filed Jun. 6, 2008.

FIELD OF THE DISCLOSURE

This disclosure relates generally to the production of sterile therapeutic medium such as sterile surgical slush for use in surgery.

BACKGROUND

Devices for producing sterile saline slush are known in the art. Sterile saline slush is used in a variety of surgical applications to slow organ and tissue metabolic rates thereby protecting organs from irreversible tissue damage during cardiac, neurological organ transplant, vascular, urologic and other complex surgeries. It is important that the slush has as smooth, spherical a configuration as possible to ensure atraumatic slush without sharp crystal edges that could puncture or damage human flesh or organs. The slush should have a substantially uniform consistency to maintain optimal thermodynamic cooling performance.

In both the surgical and non-surgical methods, slush production depends on the same basic thermodynamic phenomena. As ice grows from water that contains "impurities" the water produces a crystal matrix with the "impurities" dispersed into the interstices of the matrix. The term "impurities" are used because of the way they affect the water crystal matrix, however, they are often desirable and necessary components. In the case of non-surgical slush for drinks, the "impurities" are things like sugar and flavor mixes. In the case of surgical slush the "impurity" is salt. The impurities also provide nucleation sites that allow ice crystals to initially form. During the process of freezing a stagnant container of water with impurities, a boundary layer of slush (ice crystal in a fluid mixture) can form between a solid ice layer and a liquid water layer.

If during the freezing process the fluid mixture is mechanically agitated, small crystal formations are generated at the nucleation sites but size growth of the crystal matrix is inhibited because mechanical agitation prevents larger crystal growth. When these small crystals are suspended in the bulk fluid they form a slurry or slush. Mechanical agitation also helps keep the bulk fluid temperature more consistent and helps reduced large crystal growth that would otherwise occur at the fluid boundary (i.e. surface or container walls) where heat is typically being transferred out of the fluid.

In some prior art devices fluid is contained in a basin lined with a drape. Mechanical agitation of the fluid is provided by continually flexing the drape by lifting the drape from below with a pin or arm. The top of the basin is open to ambient air and the fluid is cooled via the metal walls and bottom that supports the drape. With this arrangement, flexing of the drape is essential to prevent large crystal formation in the fluid that is contact with the drape where heat is being transferred away from the fluid. The drape flexing also needs to be sufficient to keep the bulk mixture consistent and to keep the crystal suspended in the slush mixture. However, the need for aggressive mixing needs to be balanced with the need to maintain the integrity of the drape boundary because the drape also serves as a sterile barrier.

The integrity of the sterile field is very important during surgery. Any breach that might indicate that the sterile field has become contaminated is taken very seriously. A breach that is undiscovered for a period of time is especially troublesome as it is difficult to assess when the breach was created and whether it caused the patient to be exposed to contaminants while vulnerable during surgery. Thus it is no wonder that there may be grave concerns about the ongoing potential for breaches in the sterile field maintained by sterile drapes.

Other methods of creating slush had other shortcomings. One such method called for placing bags of sterile saline in freezers to freeze the sterile saline solution and then smashing the bag with a mallet to create slush. Such a method has a number of shortcomings including the risk of forming jagged ice crystals.

Another method called for the use of a frozen metal basin and chilled alcohol. This method involved pouring sterile saline inside the basin and scraping the side of the basin until sufficient slush is collected. The method produces slush, but is time consuming and resource intensive. Such a process does not scale well to provide a device that creates and maintains a significant amount sterile surgical slush.

SUMMARY OF THE DISCLOSURE

The present disclosure includes information about methods and apparatus for producing saline slush for surgical applications. Ideally, the slush produced is atraumatic slush that has been created through a process that reduces the sharp edges and produces smaller spheroid shaped pieces of slush rather than large frozen crystals.

One aspect of this disclosure teaches producing surgical saline slush in a rigid or semi-rigid, high integrity, sturdy container that resists punctures and leaks to better maintain a sterile barrier and does not rely on having on external object placed in the fluid to mix the slush. One type of sturdy container would be a container that could be sterilized and re-sterilized for several sterilization/use cycles. A container that is adapted for many sterilization/use cycles may be made of a durable material such as a metal. Another type of sturdy container is a pre-sterilized single use container. Such a single use container may be made of a suitable polymer to hold down costs.

Slush is agitated within the slush bottle. Slush bottle features are discussed which agitate and condition slush for use in medical procedures. The slush bottle may be rotated using a pair of rollers. A slush station may have one or more compartments for the production of slush and a basin shell for maintaining slush as slush in a basin. Specialized techniques for a vertical slush bottle are discussed. This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that arise from this application.

Other systems, methods, features, and advantages of the disclosed teachings will be or will become apparent to one with skill in the art upon examination of the following figures and detailed description. It is intended that all such additional systems, methods, features and advantages be included within the scope of and be protected by the claims that are ultimately associated with this disclosure through the use of one or more non-provisional or non-United States patent applications that claim this disclosure as a priority document.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

Figure 1:
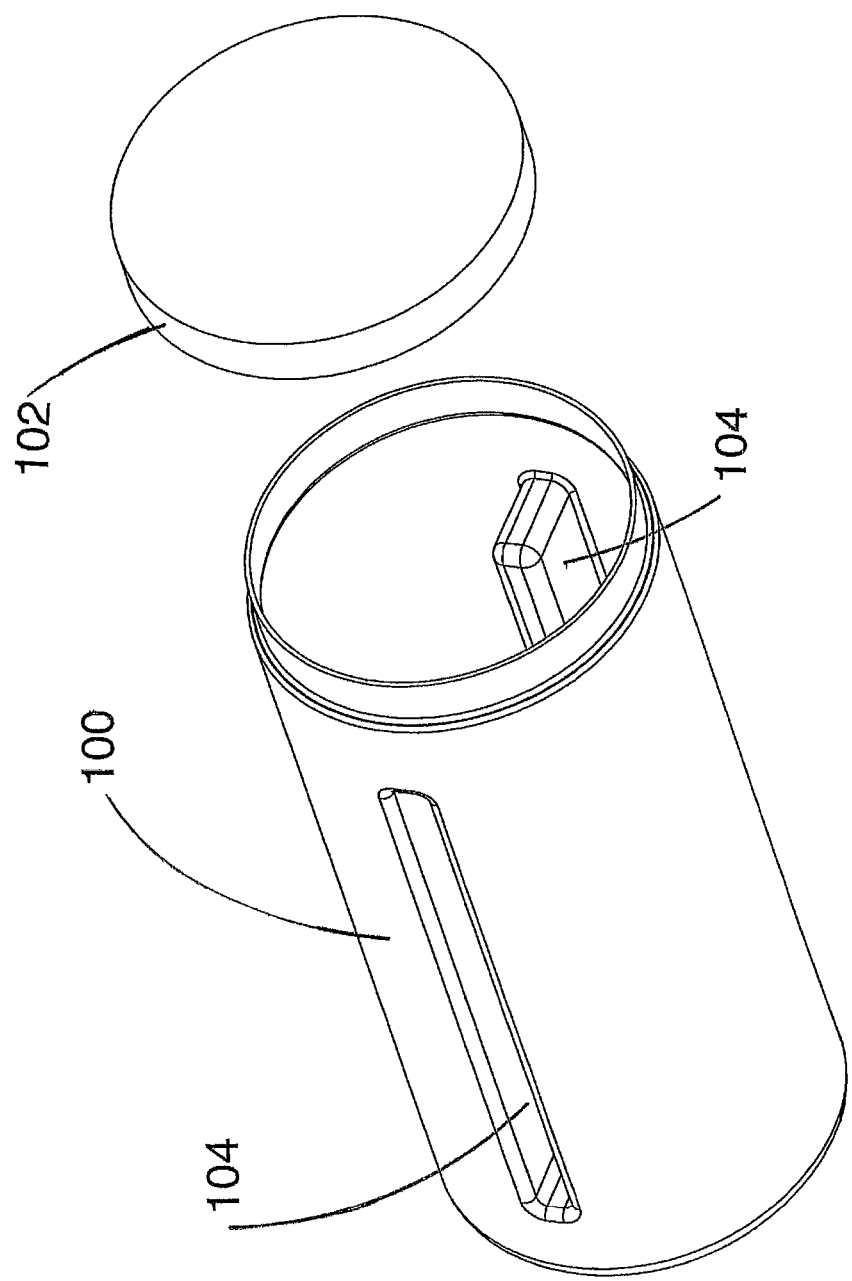
FIG. 1: Perspective view of a slush bottle and cap.

FIG. 1 illustrates a slush bottle 100 with a removable cap 102. The slush bottle 100 has a large mouth opening. The large mouth opening could be implemented with threads (not shown) for mating with corresponding threads (not shown) in the removable cap 102. Other reversible fastening techniques known to those of skill in the art could be used. Thus, bayonet fittings, snap tops, and other fastening methods, with or without the use of a gasket could be used. Implementations that use a slush bottle oriented away from horizontal and use less liquid so that the liquid does not reach the lid may have less stringent requirements for the lid.

The aspect ratio and the shape of the slush bottle may come in a variety of forms. No particular expectation should be inferred from the use of the word "bottle" in lieu of a more amorphic term like container. As long as the item has an inside that can be used to receive saline and allow the removal of surgical slush, then the shape may be viable (perhaps far from optimal) as a "bottle".

During operation, the slush bottle 100 is initially filled with a liquid saline solution and has the removable cap 102 tightly secured. In this context, "filled" means filled to an intended fill line rather than totally filled as having the slush bottle only partially filled is useful in promoting the tumbling action described in more detail below.

The slush bottle 100 and cap 102 can be made of any of a number of conventional polymers having the appropriate mechanical properties and the ability to withstand the desired sterilization regime. An example of a suitable polymer material is polypropylene. (A reusable slush bottle may have a lid that is made of the same metal as the slush bottle or at least having a similar coefficient of thermal expansion.) The saline solution that is used is conventional sterile saline solution of the type used in surgical procedures whether heated to approximately body temperature or used at some other temperature.

An alternative that may be used with this slush bottle or with others having an appropriate shape (see various alternative slush bottles disclosed below) is to use a sterile plastic liner for the slush bottle or lid or both. The use of a sterile plastic liner would allow a metal or other durable bottle or lid to be used with an inexpensive sterile plastic liner. The liner would need to be sufficiently durable for the task and would need to avoid having large amounts of excess liner protruding out of the bottle/lid assembly to avoid entanglement.

Two fins 104 (some might call them ribs) are formed into the side wall of the slush bottle 100 and protrude into the interior of the slush bottle 100.

Figure 2:
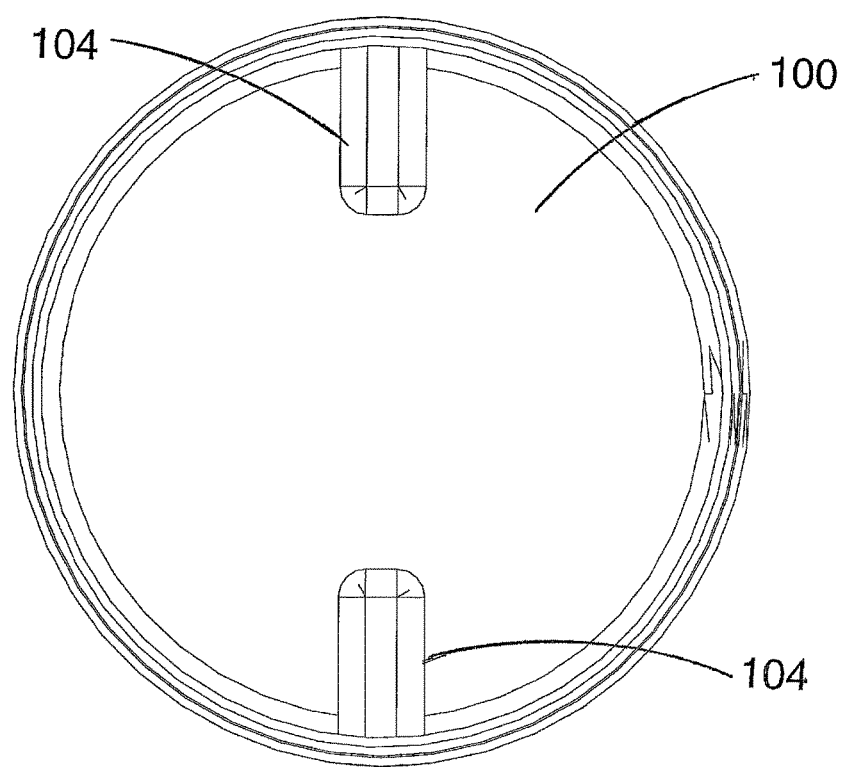
FIG. 2: Top view of a slush bottle showing the interior.

FIG. 2 shows a top view of the slush bottle 100 with interior fins 104. The slush bottle 100 shown in FIGS. 1 and 2 has two fins 104; however, one fin or more than 2 fins are also possible. While the two fins shown in FIGS. 1 and 2 are identical, the do not have to be. The fins may optionally have one or more gaps in the fin. When using fins with at least one gap, not all fins need to have gaps and not all fins need to have the same arrangement or spacing of the gaps. As the slush bottles rotate, the gaps in the fins will cause movement of the slush through the gaps relative to the slush that is lifted by the fin and tumbled. This will add another aspect to the stirring of the slush. Likewise the fins 104 do not need to be evenly spaced around the perimeter of the slush bottle 100. For example, the two fins 104 shown in FIG. 2 could be spaced a hundred degrees apart rather than being 180 degrees apart. Bottles with shapes other than cylindrical (i.e. oval, square, rectangular, etc.) are also possible.

While the fins shown in FIGS. 1 and 2 extend inward from the side wall, a slush bottle may optionally have one or more bottom protrusions that extend upward from the bottom of the slush bottle (toward the lid). To the extent that the protrusion is at least partially non-symmetric with the center axis of the bottom of the slush bottle, the protrusion will add another dimension to the mixing of the slush, will potentially add another surface for the falling slush to strike and may provide a way to enhance the cooling of water to form slush to the extent that cooled air is present in the protrusion extending into the slush bottle.

While not strictly required, it is felt that a fin that is hollow and open to the air external to the slush bottle will help cool air enter the fin and augment the cooling. A secondary benefit of the fin and a design consideration for the fins is the hollow fin may provide a finger hold for a user that is picking up a frosty slush bottle from the slush making device. The hollow fin may help the user have a reliable grip on the slush bottle while lifting, removing the cap, and pouring the slush.

The slush bottle geometry with at least one interior fin allows slush to be directly produced in the enclosed slush bottle interior when the slush bottle is placed in a cold enough environment and the slush bottle is agitated. Agitation could come from rotating the long axis of the slush bottle while the axis is at or near horizontal. The range of acceptable tilt angles from horizontal upward would be a function of a number of factors. Unless the bottom has one or more protrusions, it may be beneficial for the saline water to be loaded into the slush bottle so that at least some air can reach the bottom of the slush bottle so that there is some level of tumbling all the way to the bottom. The deviation from horizontal that would work would be a function of the aspect ratio of the slush bottle and the relative height of the fill line of a slush bottle relative to the height of a slush bottle when placed in a vertical position.

One of skill in the art will appreciate that if the slush bottle lid provided a water tight seal and the slush bottle could be retained in the slush creating device while the slush bottle is rotated that the slush bottle lid could be lower than the slush bottle bottom thus below horizontal.

In the configuration shown in FIG. 1, the fins 104 introduce mechanical agitation to the solution by carrying fluid and/or slush up the sidewall during rotation. Once the fin rotates above the horizontal plane, the fluid and/or slush the fin was carrying runs or falls back into the bulk mixture. (Note that if the fill level is above the horizontal plane the run-off for liquids may be delayed until the fin is above the waterline but slush will move relative to other slush in many instances when the fin gets above horizontal.) This agitation keeps the solution mixed and tends to promote an even temperature distribution. This agitation also breaks up larger crystal matrices to promote the creation and maintenance of a fine slush mixture (as opposed to coarse). Falling material works to breaks off crystals that form along the slush bottle interior.

The amount of agitation provided to the slush may be reduced if the slush bottle 100 is positioned in a vertical orientation in the slush bottle carriage (or even 180 degrees rotation from vertical). Thus in most instances the slush bottle carriage should be oriented so that the slush bottle is neither substantially vertical nor substantially upside down.

Having a slush bottle opening that is large relative to the cross section of the slush bottle is desirable. The large mouth opening of the slush bottle makes it easy to pour the slush out of the container. A small opening (relative to the cross section of the slush bottle) might encourage the fine, loosely packed slush to become compacted as the slush passes through a reduced cross sectional area as the slush cannot easily move from a larger cross sectional area to a smaller cross sectional area without being compacted. If the slush gets compacted, the slush tends to behave more like a solid and is therefore even harder to make the slush exit through a small opening.

Figure 3:
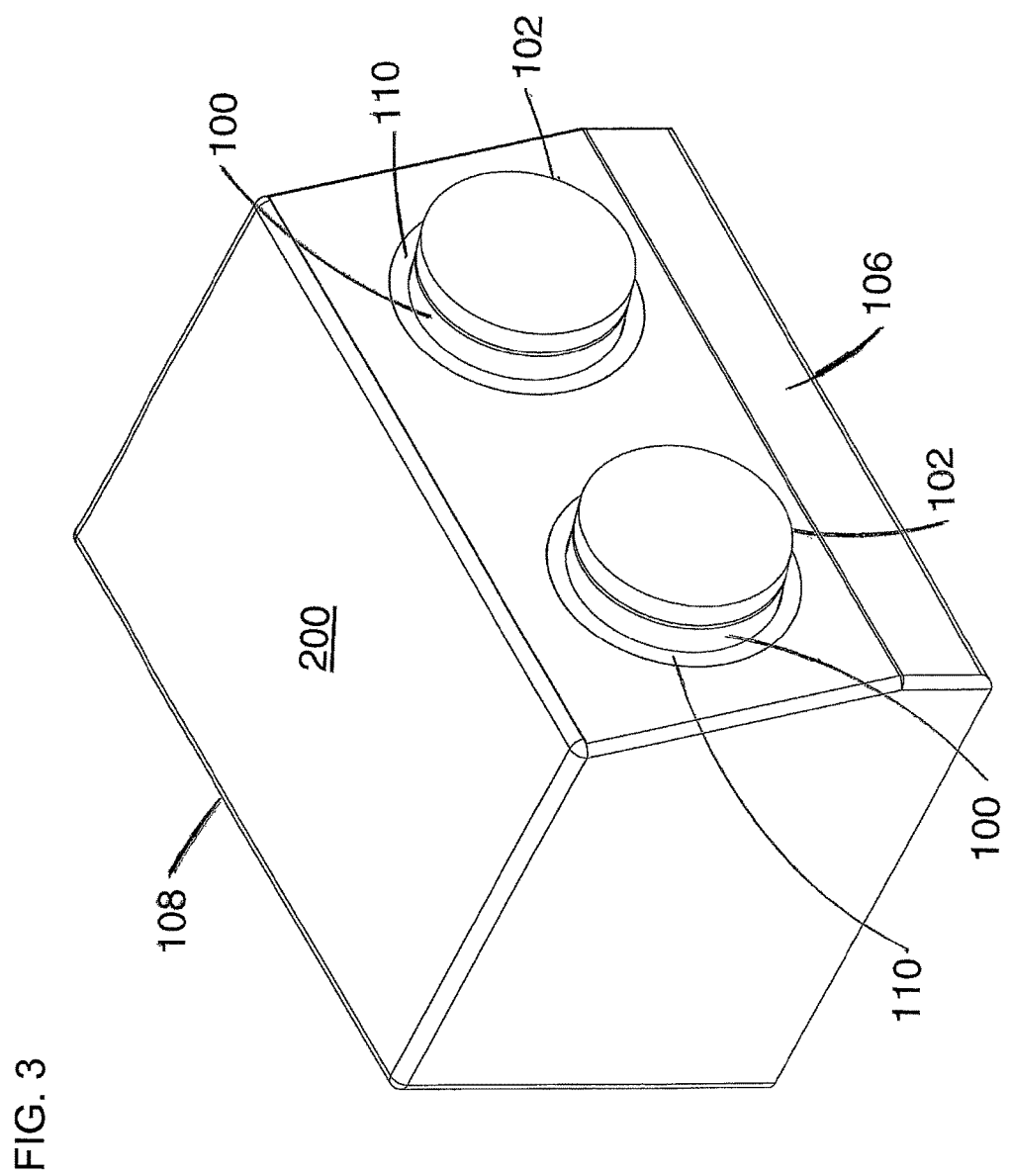
FIG. 3: View of slush production device with covers.

FIG. 3 illustrates an example embodiment of a device 200 that can rotate and cool a slush bottle 100 with a cap 102 in the manner described above so as to turn the enclosed fluid saline solution into a slush mixture. While it is important that the interior of the slush bottle and the water/slush mixture remain sterile, it is not important that the outside of the slush bottle remain sterile during the chilling process. Thus, it is not important to design or maintain the device 200 so that the interior of the device remain sterile.

In this embodiment, the device 200 is designed to hold two slush bottles 100 that are slid into the device 200 through rotating outer rings 110. The rotating outer rings 110 can rotate relative to the stationary outer support frame 106. The device 200 is enclosed with a top cover 108 (also known as a housing).

While the device 200 can receive and chill two slush bottles 100, devices (not shown) may be adapted receive only one slush bottle, or conversely may be adapted to receive and chill more than two slush bottles. In most instances, a device with an open cavity that allows chilled air to flow around multiple slush bottles will need to have an empty slush bottle inserted into each slush bottle hole or some sort of cover in order to reduce the loss of cold air out of an opening that does not have an inserted slush bottle.

An alternative would be to have separate cooling for separate compartments so that if a multi-bottle device had only one slush bottle inserted for cooling, only the compartment around that slush bottle would be cooled and the cooling going to that compartment would not travel by convection into one or more adjacent compartments that do not have a slush bottle to cool.

The device 200 in FIG. 3 is shown as a stand-alone device. One of ordinary skill in the art can appreciate that this functionality may be built into a device with other functionality such as a device intended to maintain sterile fluid at an elevated temperature for use in medical procedures. See for example commonly assigned U.S. Pat. No. 7,128,275 for Liquid Warming Device with Basin or Patent Application Publication No. 2006/0289016 for Open Access Sleeve for Heated Fluid Units.

Figure 4:
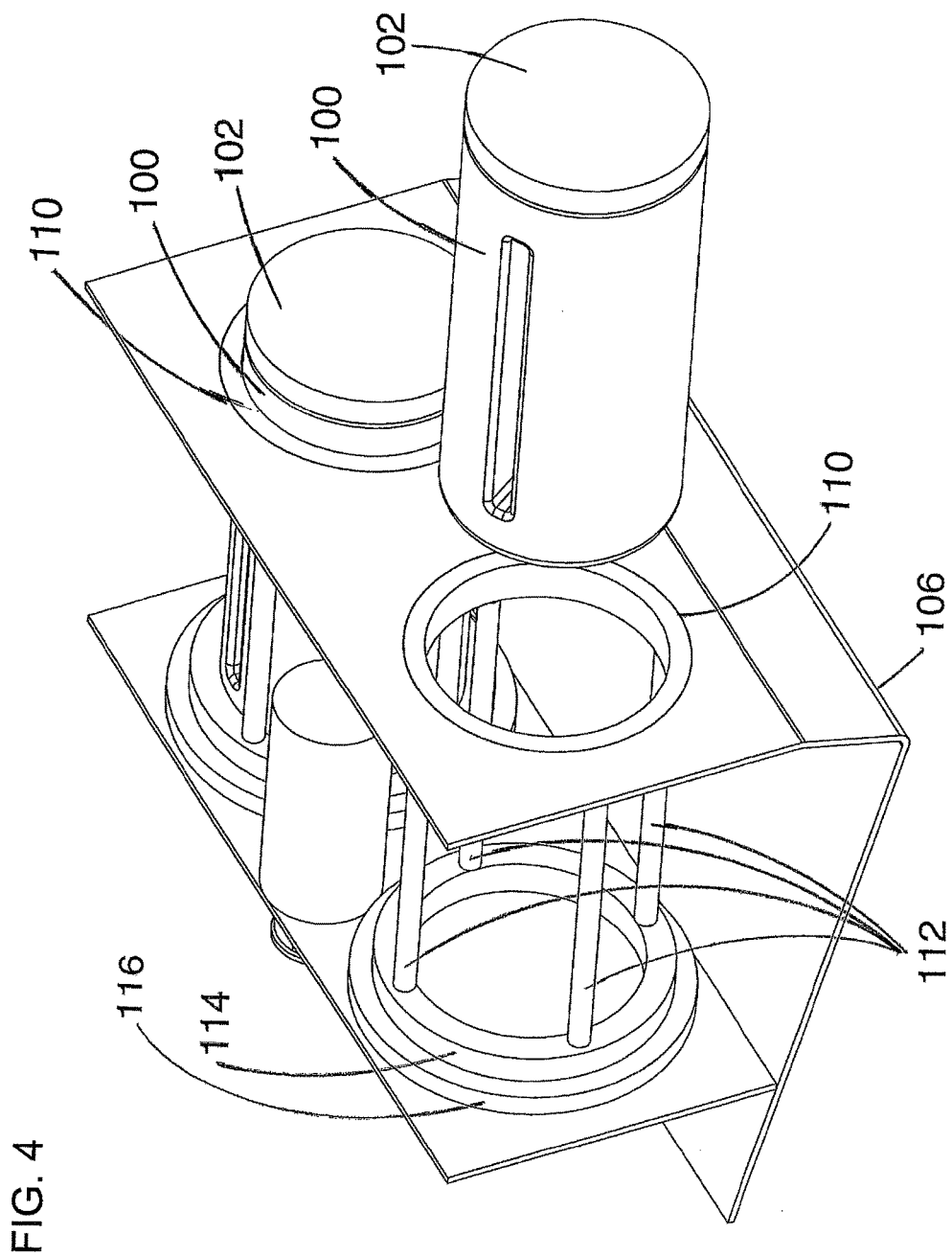
FIG. 4: Front perspective view of device without covers.

FIG. 4 shows the device 200 with the top cover 108 removed and with one of the slush bottles 100 withdrawn from the device 200. One end of each of four connector rods 112 is attached to the back side of the rotating outer ring 110. The other end of each of the four connector rods 112 is connected to the rotating bottom ring 114. The rotating outer ring 110, the connector rods 112, and the rotating bottom ring 114 all rotate together and are supported by a bottom bearing 116 on one side and a front bearing 118 (shown later in FIG. 5). The bottom bearing 116 is mounted in the back support plate 120 and the front bearing 118 is mounted in the outer support frame 106.

Figure 5:
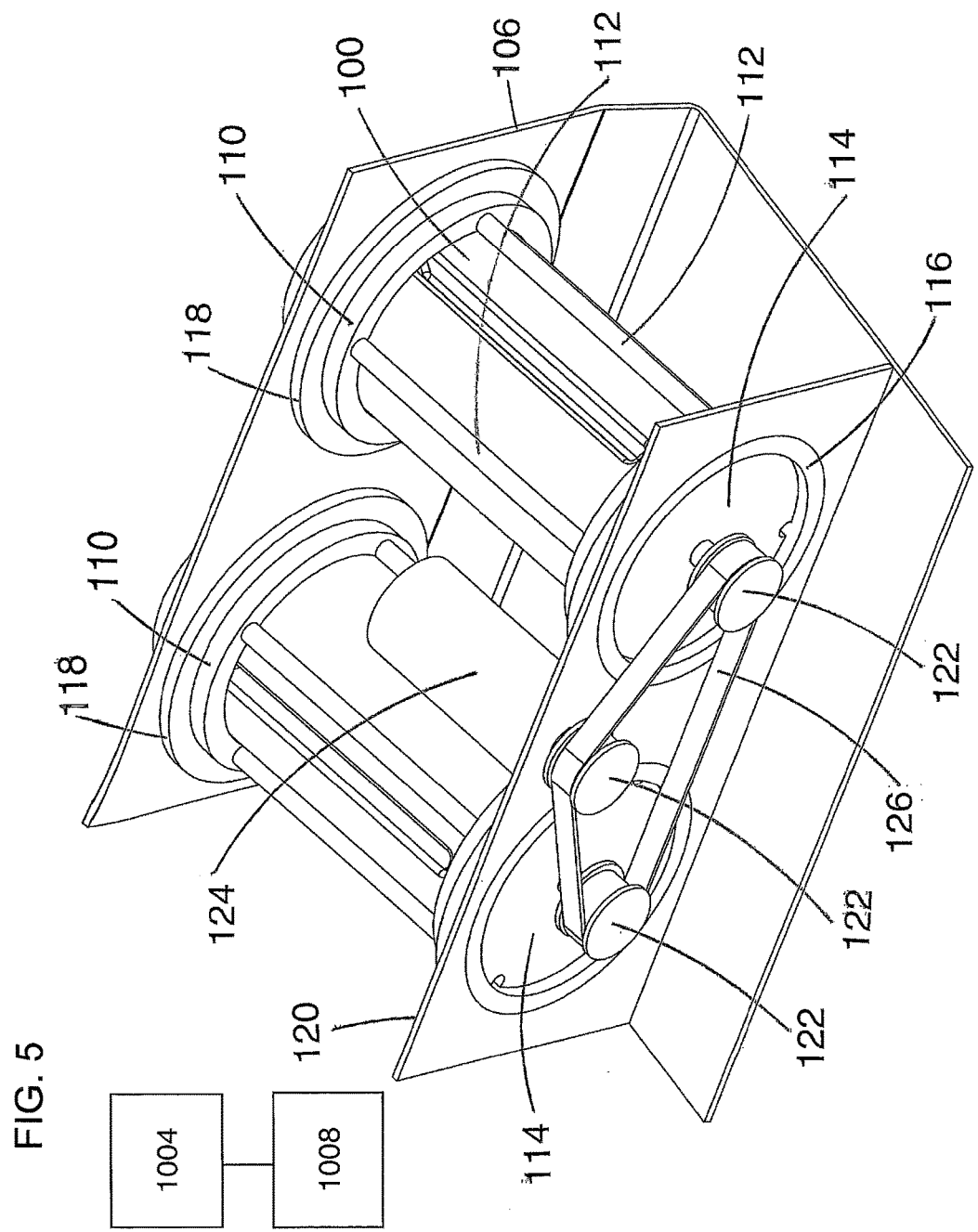
FIG. 5: Back perspective view of device without covers.

FIG. 5 is a view of the device 200 from the back. The front bearing 118 described above can be seen mounted in the outer support frame 106 and holding the rotating outer ring 110. A drive pulley 122 is attached to both rotating bottom rings 114 and to the drive motor 124. The drive motor 124 is mounted to the back support plate 120. A drive belt 126 is looped around the three drive pulleys 122. Visible in this figure are some of the notches that provide access to the fasteners used to retain the individual connector rods. These details are routine to those of skill in the art and need no further discussion.

When the drive motor 124 is turned on it causes both rotating bottom rings 114 to rotate via the drive belt 126 and drive pulley 122. This in-turn cause the slush bottles 100 to rotate because they are supported by the rotating bottom ring 114, the connector rods 112, and the rotating outer ring 110 which are being driven by the drive motor 124. The slush bottles may be rotated at a relatively slow speed so as to facilitate the dropping of material to agitate and to minimize any centrifuge effect that would impede such agitation. Typical rotation speeds would be in the range of 10 to 30 slush bottle rotations per minute, however, a broader or shifted range of speeds may be adequate in some situations.

One of ordinary skill in the art will appreciate the minor modifications necessary to the device 200 to receive and rotate slush bottles with a cross section that is something other than round. One of ordinary skill in the art will recognize that other choices and arrangement of components could be made in order to effect the rotation of the slush bottles. For example the driver motor 124 could be located outside of the enclosed space.

The individual components of the cooling system 1004 (FIG. 5) along with the interior covers and insulation are not shown in the figures because they would obscure the drive and support components. The cooling system's purpose is to provide chilled air to surround the slush bottles and to chill the air below the freezing point of the saline water within the slush bottles. The cooling system may include one or more devices such as fans to circulate the cooled air to promote the rapid cooling of the saline in the one or more bottles. Those of skill in the art will appreciate that a range of cooling systems could be used including but not limited to a standard compressor type system or a solid state Peltier cooling system.

The cooling system regulates the temperature around the slush bottles to within a specified range to allow slush to be produced and maintained. The control system 1008 may simply seek to maintain the air within the device at a particular target temperature that is at or slightly below the freezing point for sterile saline solution of a particular salinity. A more sophisticated system would have an initial target temperature that is well below the freezing point to expedite the initial production of slush but then have a separate maintenance temperature intended for use when the slush is ready. This maintenance temperature could be at or slightly below the freezing point (to compensate for thermal losses and energy input to the system). As the slush will continue to freeze slowly at this freezing point, it may be useful to build in a capacity for the target temperature to drift above and below the freezing point (as with a normal two temperature control scheme that results in a saw tooth temperature profile).

In some instances, increasing the level of agitation, perhaps by increasing the speed of slush bottle rotation may provide a wider range of temperatures that may be used to maintain the slush as slush.

The device 200 may optionally have a stop button to stop the rotation of the slush bottles. This stop button may make it easier to remove a slush bottle from the slush making device.

Additional Views of the Slush Bottle.

FIGS. 6-9 show the slush bottle 100 from FIGS. 1 and 2 from four view separated by 90 degrees.

Figure 6:
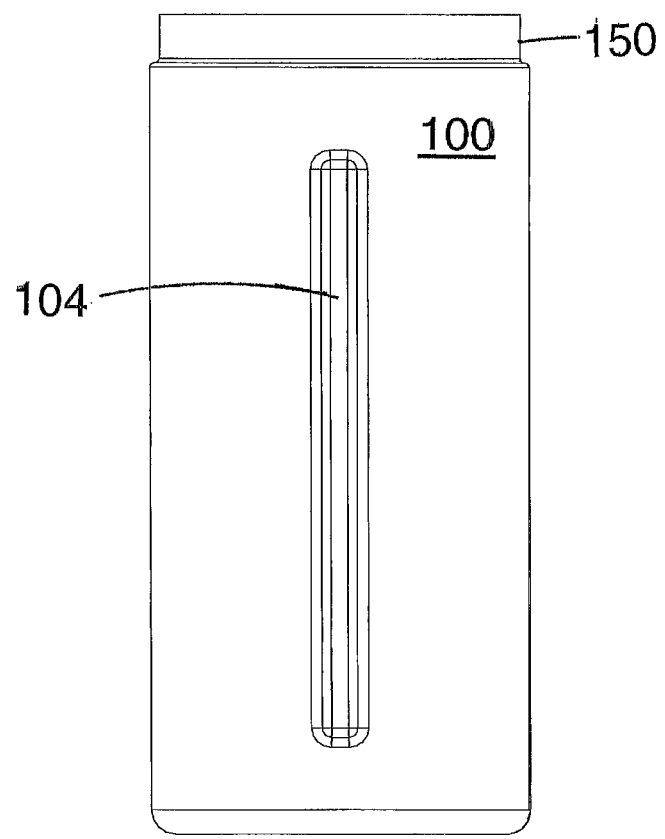
FIG. 6: Side view of the slush bottle of FIGS. 1-4.

FIG. 6 shows a side view of the slush bottle 100 with the interior of one fin 104 visible. The portion 150 of the slush bottle that receives the cap (seen in FIG. 1) is visible.

Figure 7:
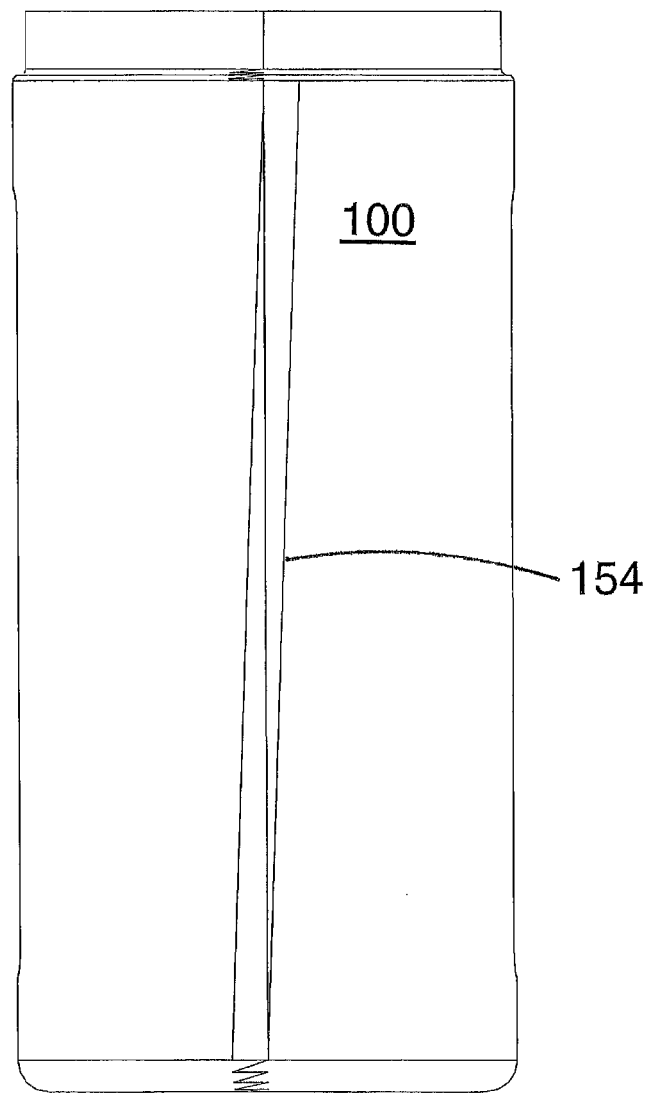
FIG. 7: Side view of the slush bottle 90 degrees offset from FIG. 6.

FIG. 7 shows a side view of the slush bottle 100 90 degrees offset from FIG. 6. Visible in this figure is a representation of a bottle seam 154. The actual bottle seam may not appear as shown in FIG. 7 and may not be readily apparent to an untrained eye.

Figure 8:
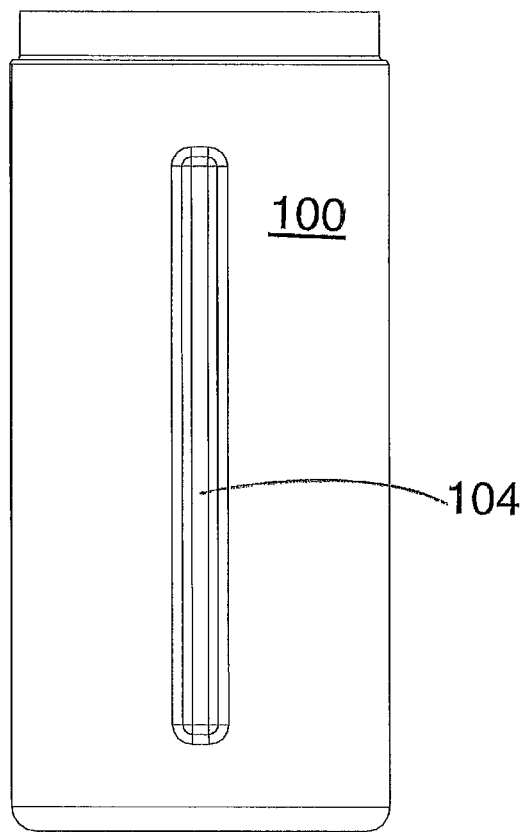
FIG. 8; Side view of the slush bottle 90 degrees offset from FIGS. 7 and 180 degrees offset from FIG. 6.

FIG. 8 shows a side view of the slush bottle 100 90 degrees offset from FIG. 7. FIG. 8 is identical to FIG. 6 because this particular implementation of the slush bottle has two identical fins offset by 180 degrees.

Figure 9:
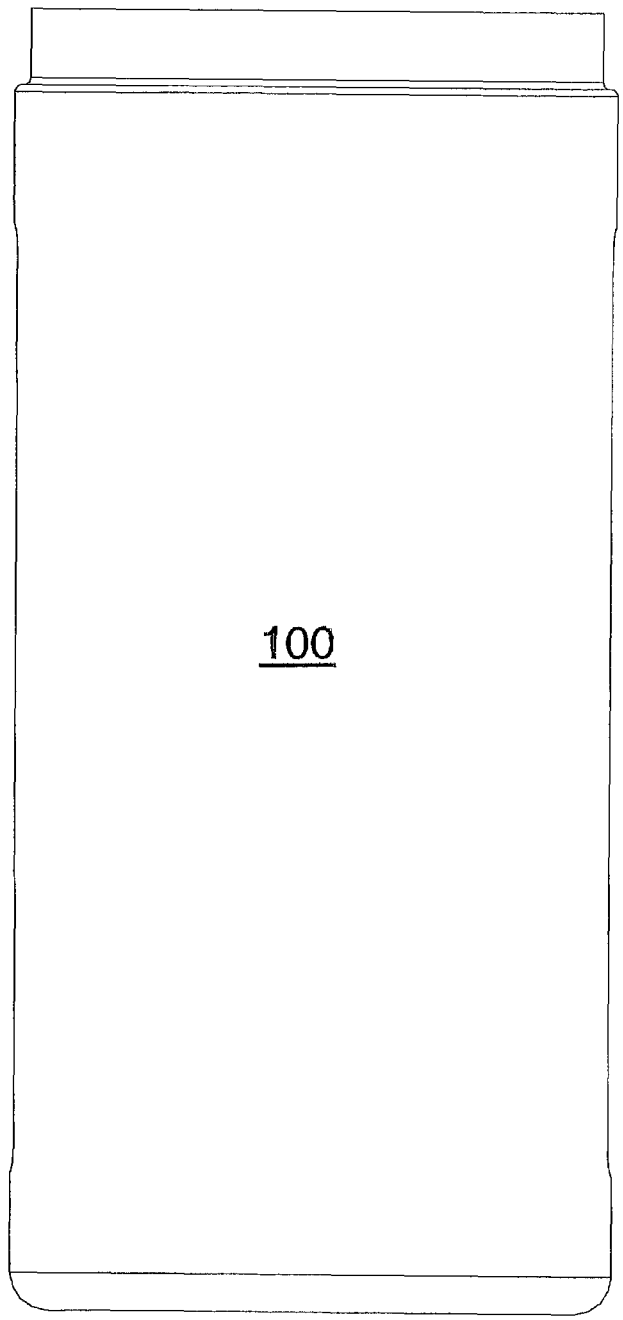
FIG. 9: Side view of slush bottle 90 degrees offset from FIG. 8.

FIG. 9 shows a side view of slush bottle 100 90 degrees offset from FIG. 8.

Figure 10:
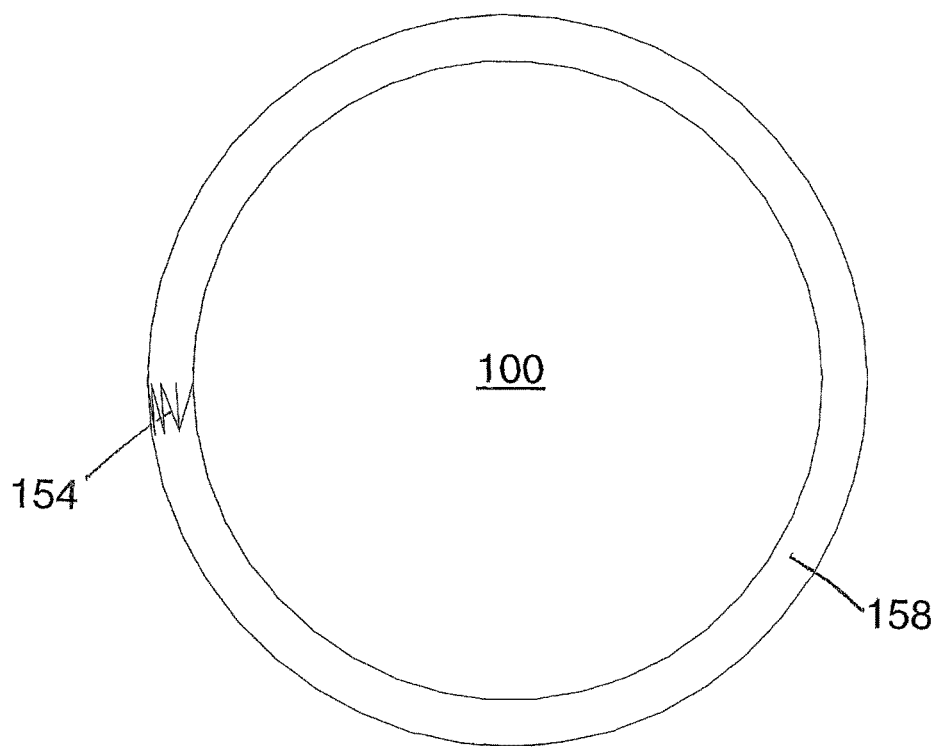
FIG. 10: A bottom view of slush bottle shown in FIGS. 1-10.

FIG. 10 shows a bottom view of slush bottle 100 including beveled rim 158 and the bottom of the representation of the bottle seam 154.

ALTERNATIVES, VARIATIONS, and EXTENSIONS

Cabinet Doors.

The slush production device 200 shown in FIGS. 4-6 has the end of the slush bottle 100 and the slush bottle cap 102 protruding beyond openings in the device top cover 108 (also known as a housing). The slush bottle 100 and slush bottle cap 102 are thus part of the effective border that holds the chilled air within the device 200. One of ordinary skill in the art will appreciate that the device could be modified to have a larger enclosed volume that is accessed through cabinet doors or other ready access options known in the art. Thus, the cabinet doors would form the barrier between the chilled air used for cooling and the ambient air in the hospital. Note that if the slush bottle was contained within a housing with closed cabinet doors, one could conceivably maintain a sterile state within the housing and operate the slush making device using a slush bottle without a top. Obviously the slush bottle orientation and fill level would need to be adjusted that that saline would not splash out the top during slush operation. This variation is unlikely to be widely adopted.

Non-Centerline Center of Rotation.

The slush production device 200 shown in FIGS. 4-6 has a center of rotation for rotating the slush bottle 100 that runs through the axial centerline of the slush bottle 100. This configuration may be preferred in some embodiments as it would tend to provide a smooth uniform agitation. Other embodiments may use a center of rotation that runs through something other than the top/bottom centerline of the slush bottle. An advantage of this choice may include a more complex agitation pattern.

Multi-Angled Bottle Walls.

One of skill in the art will recognize that a slush bottle made with severe wall joint angle changes may provide much of the agitation provided by the slush bottles with fins shown above. For example, a slush bottle with the cross section of a triangle or a five or six sided star might provide adequate agitation, particularly if the slush bottle was oriented closer to horizontal to promote slush from falling from the ridges formed by the points of the star or other appropriate shape.

Saline within a Flexible Bag.

Figure 11:
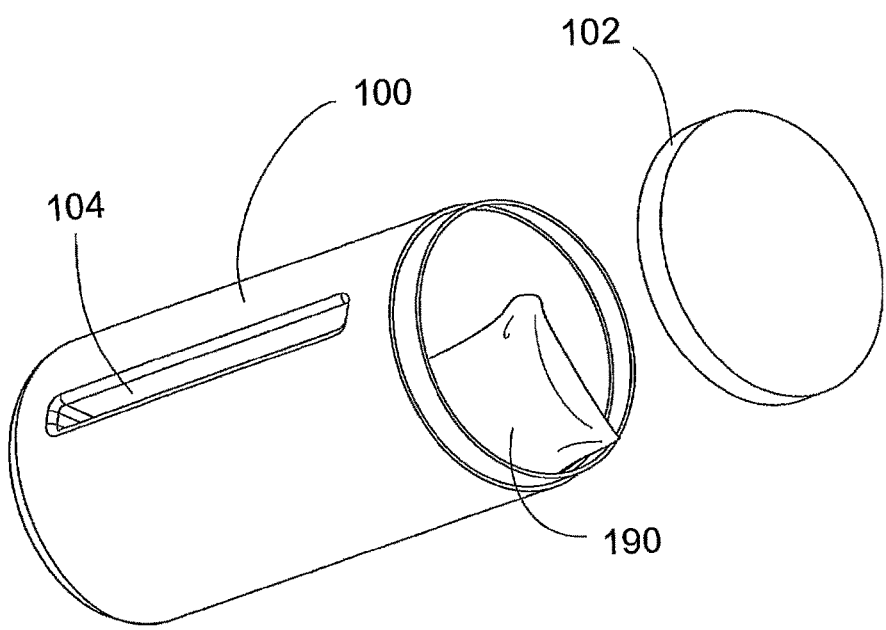
FIG. 11 shows a flexible container of sterile saline in a slush bottle.

An alternative implementation would be to place saline in a flexible container of any shape. It is probably easiest to envision a clear bag like a partially filled IV bag. Ideally the bag should not be so filled with saline as to be taut. The saline bag 190 may be placed in a slush bottle 100 as shown in FIG. 11 and tumbled as the slush bottle rotates in the slush bottle carriage. The bag would need to be sufficiently robust, including any seams and broad pour spouts to handle the tumbling within the slush bottle which may be aligned close to horizontal.

One of ordinary skill in the art will recognize that in a saline bag implementation, the slush bottle need not be removable but may be integrated within the slush producing device much like the horizontal drum of a clothes dryer.

Alternative Slush Bottles and Removable Tops

Figure 12:
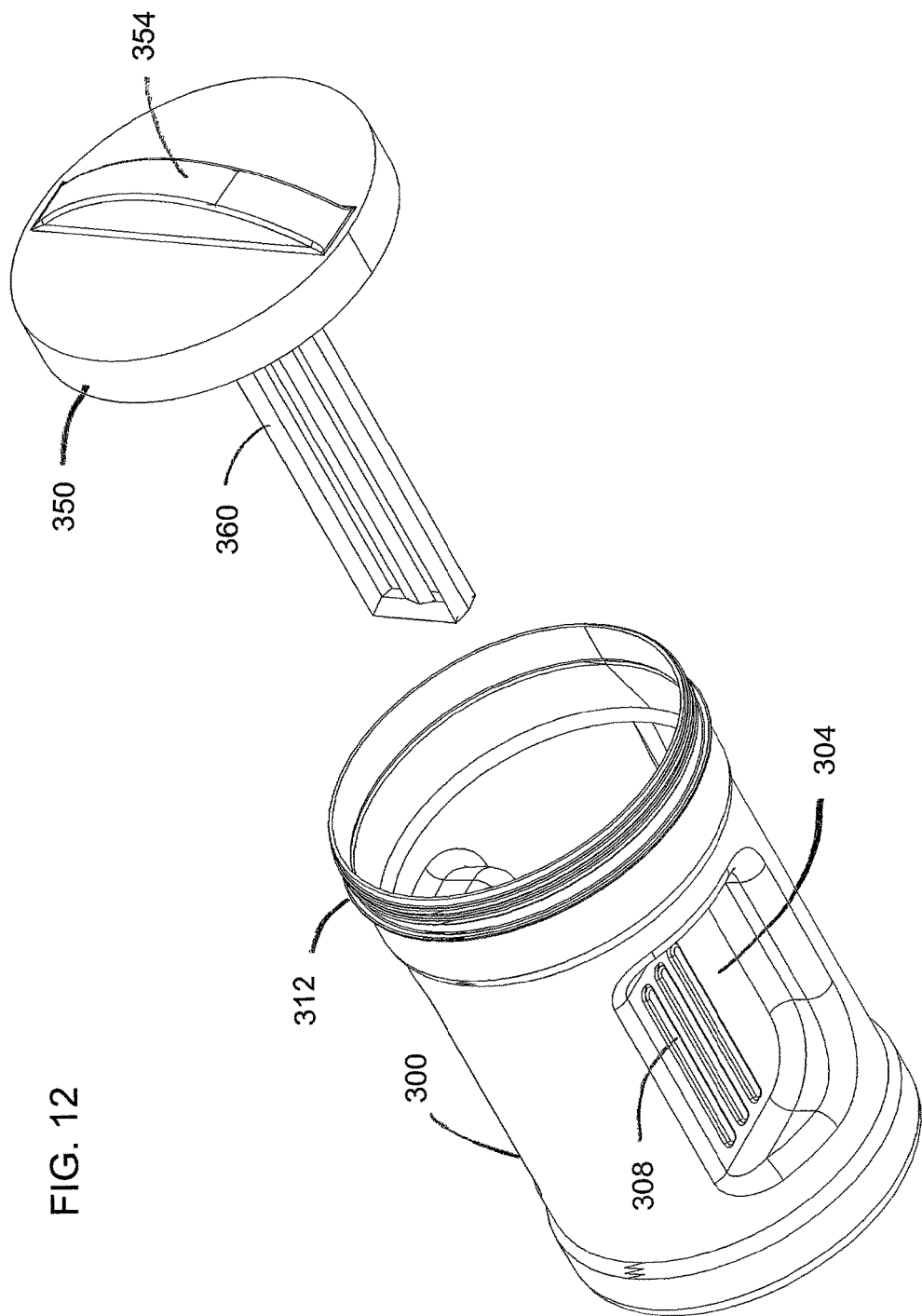
FIG. 12 shows a perspective view of slush bottle 300 with removable top 350.

FIG. 12 shows a perspective view of slush bottle 300 with removable top 350.

Visible in FIG. 12 is a pair of grip indents 304 to facilitate picking up the slush bottle 300. The grip indents 304 may be spaced to allow a user to push squeeze the pair of grip indents 304 between the thumb and fingers of the user. The grip indents 304 may include ribs 308. The grip indents 304 and ribs 308 serve as features in the side walls of the slush bottle 300 that serve to agitate slush while the slush bottle 300 is being rotated at any orientation and will serve to lift and drop slush if the slush bottle 300 is rotated at any orientation other than along the top/bottom axis of the slush bottle 300.

A set of male threads 312 may be used to mate with corresponding threads on a removable top. Thread choice is based on providing a water tight seal but yet releasing without tools even if there is ice near the threads.

FIG. 12 shows a raised ridge 354 of the removable top 350. This raised ridge 354 may be used by the user to hold the removable top 350 and to apply torque to the removable top such as would be used to thread or unthread an engagement between the removable top 350 and the slush bottle 300.

FIG. 12 also shows optional center paddle 360 described in more detail below.

Figure 13:
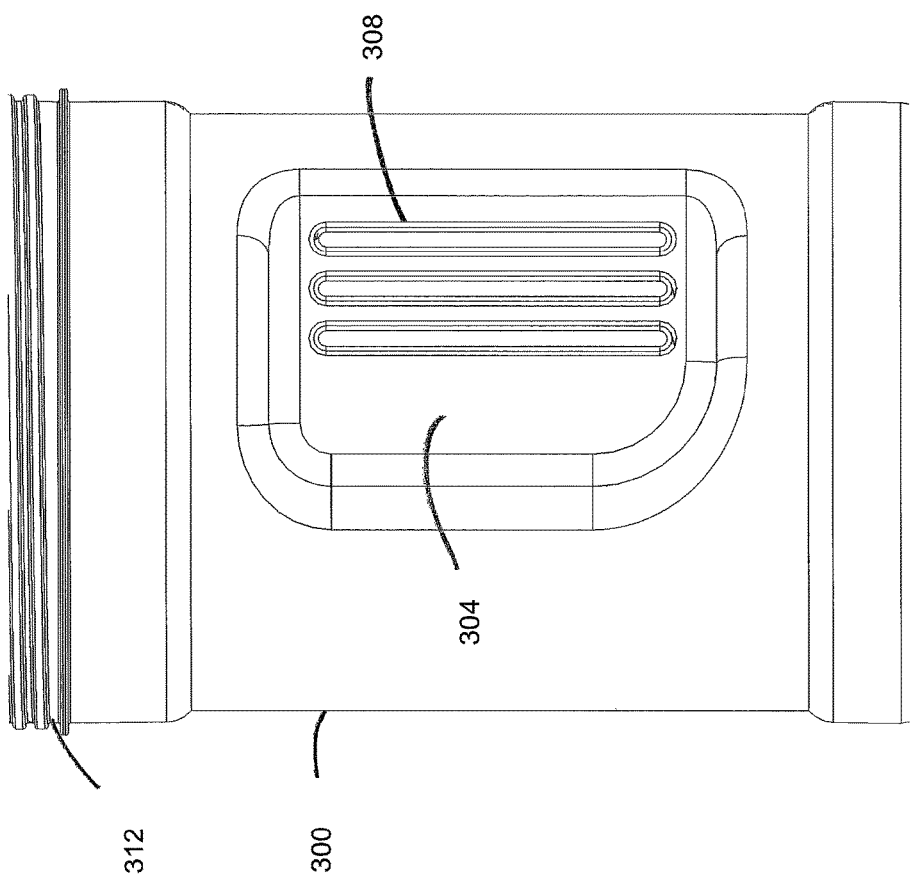
FIG. 13 is a side view of slush bottle 300 showing one of the two grip indents 304, ribs 308, and male threads 312.

FIG. 13 is a side view of slush bottle 300 showing one of the two grip indents 304, ribs 308, and male threads 312.

Figure 14:
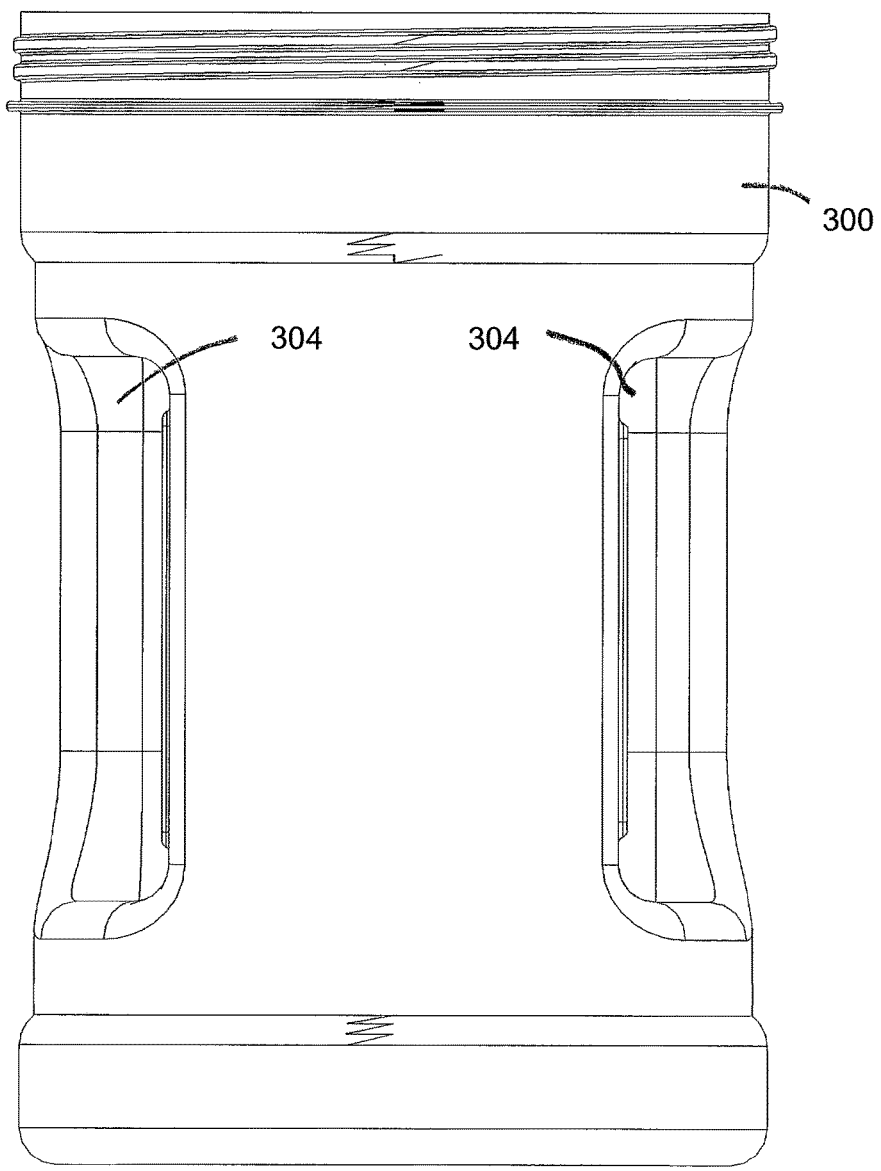
FIG. 14 is another side view of the slush bottle 300 showing the pair of grip indents 304.

FIG. 14 is another side view of the slush bottle 300 showing the pair of grip indents 304.

Figure 15:
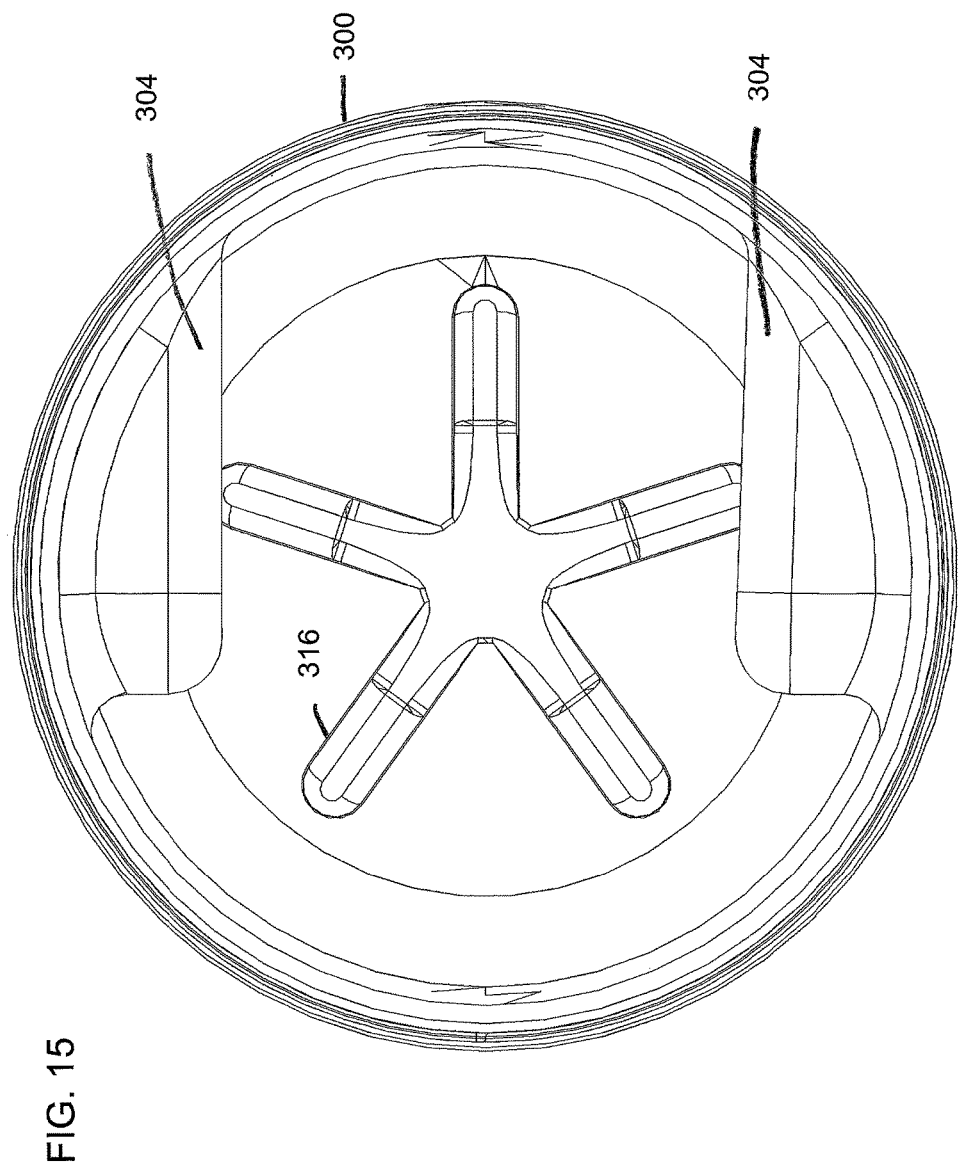
FIG. 15 shows a top view of slush bottle 300.

FIG. 15 shows a top view of slush bottle 300. Visible in this view are grip indents 304 which extend inward and optional radial feature 316 which extends up into the slush bottle interior and provides another set of features to agitate and lift slush. In this example there are five arms to the radial feature 316 but different numbers of arms could be used. The pattern of arms does not have to be symmetric. The radial feature is an example of an agitation/lift feature on the bottom of the slush bottle 300. The agitation/lift feature need not be a radial design. A series or parallel ribs could be used for the agitation/lift feature. As described below, there is an advantage in having an indentation at the axial centerline of the slush bottle 300 but this could be incorporated in a wide array of possible sets of agitation/lift features for the bottom of the slush bottle.

Figure 16:
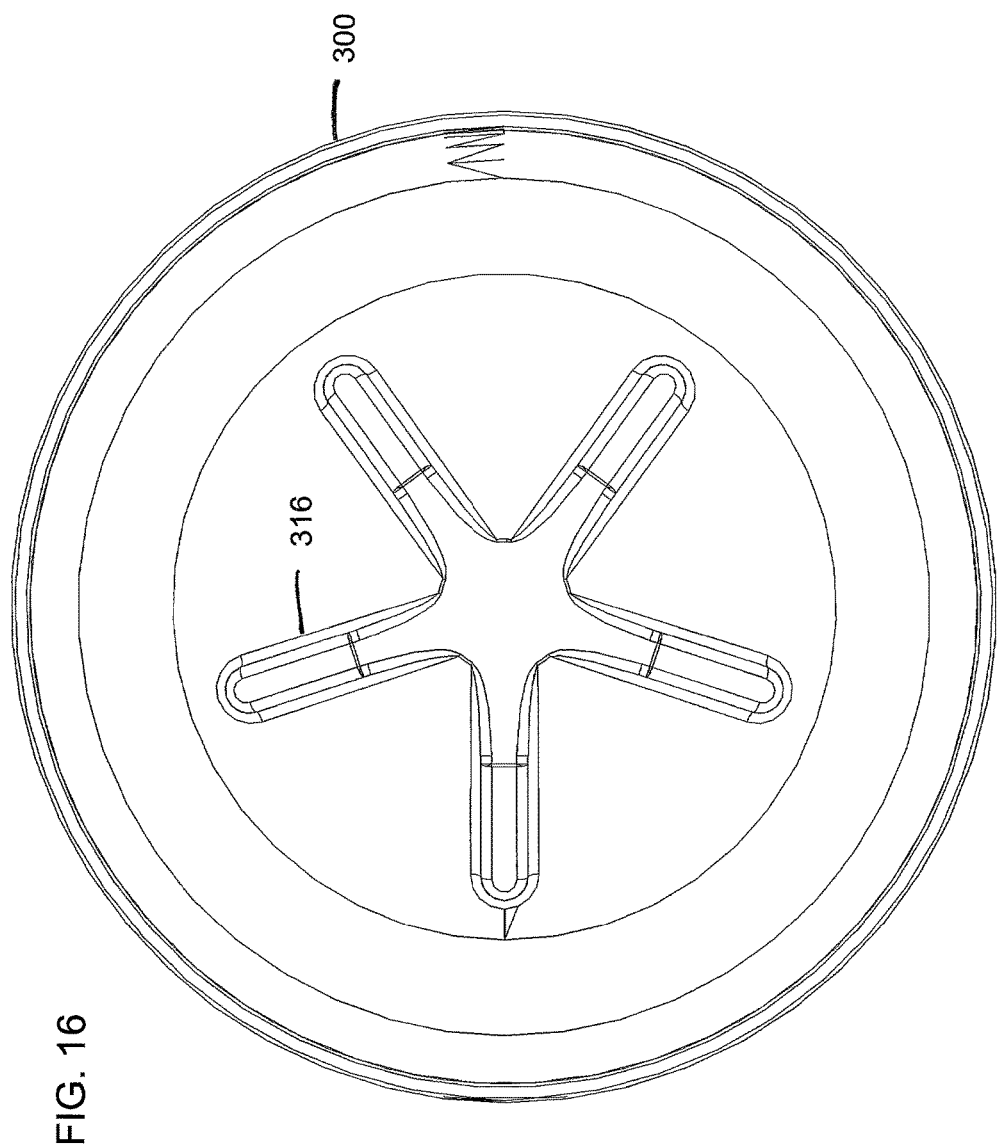
FIG. 16 is a bottom view of slush bottle 300 showing the radial feature 316.

FIG. 16 is a bottom view of slush bottle 300 showing the radial feature 316.

Figure 17:
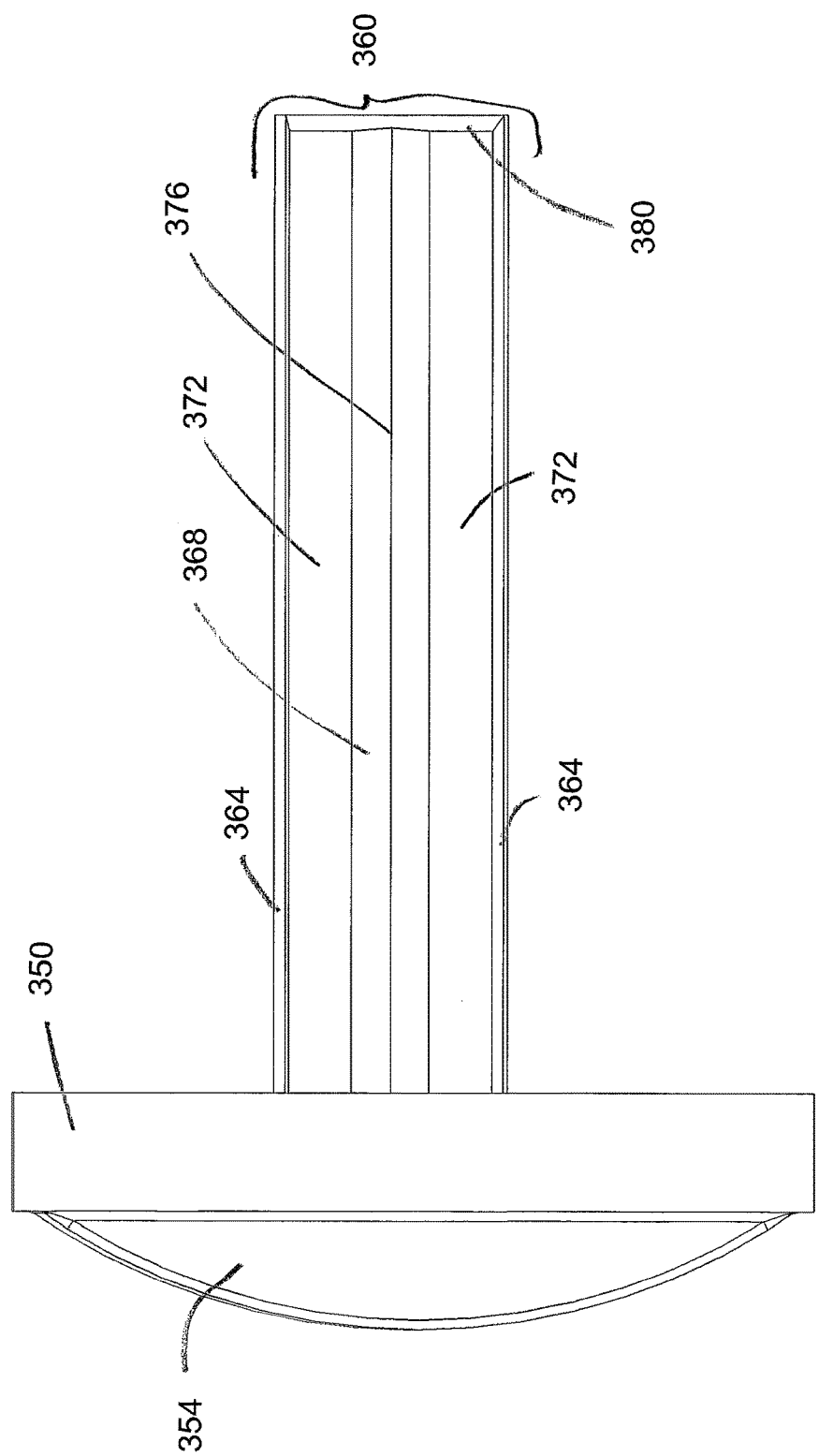
FIG. 17 is a side view of removable top 350 with optional center paddle 360.

FIG. 17 is a side view of removable top 350 with optional center paddle 360. While the center paddle may be configured in a number of ways, the version shown in FIG. 17 has an outer frame with two frame sides 364 joined by a frame bottom 380. An interior stirrer bar 368 is in the interior of the center paddle 360. There are gaps 372 between the interior stirrer bar 368 and the two frame sides 364. While only a single interior stirrer bar 368 is shown here, more than one can be used, especially for a particularly wide center paddle 360. Conversely, the interior stirrer bar 368 could be omitted leaving just one gap 372 between the two frame sides 364. The depth of the center paddle is chosen to allow clearance between the distal end of the paddle and the bottom of the slush bottle.

Figure 18:
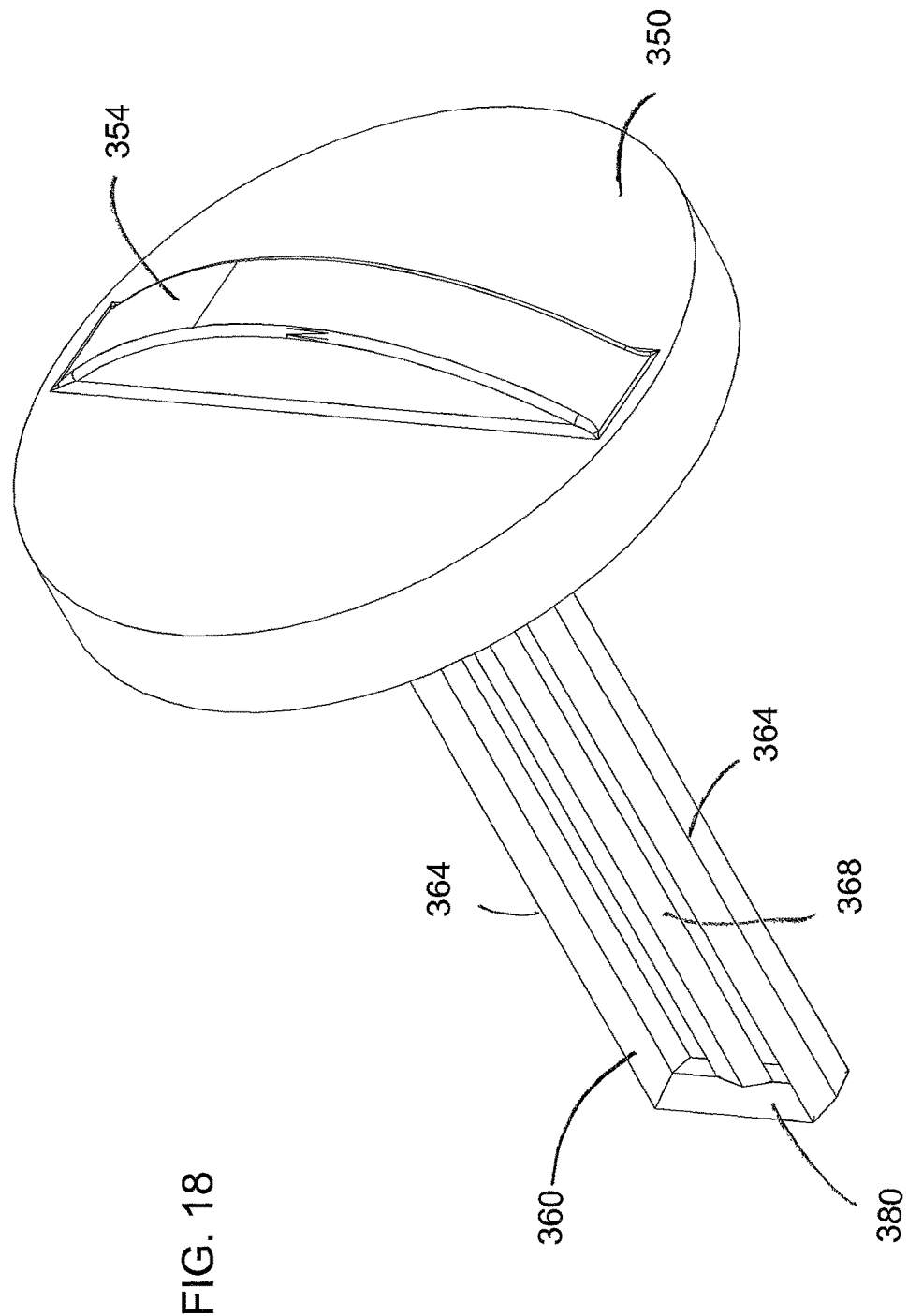
FIG. 18 is a perspective view of removable top 350 with optional center paddle 360.

While other cross sections could be used, the cross sections for the components shown in FIG. 17 are diamond shaped for frame sides 364 with the long dimension of the diamonds perpendicular to the long dimension of the frame bottom 380. The cross section of the interior stirrer bar 368 is a diamond with the long dimension of the diamond parallel to the long dimension of the frame bottom 380. An apex line 376 of the interior stirrer bar 368 is visible in FIG. 17. The cross section of the frame bottom 380 is triangular as best seen in the perspective view found in FIG. 18.

It is a design goal for the center paddle to agitate slush that might otherwise be immobile along the centerline of rotation. Thus a stirrer bar 368 is particularly useful along the centerline of rotation. The frame sides 364 work to break up loosely packed balls of congregated frozen slush that would otherwise tend to grow from a nucleation site. Thus, a knife-like shape to the frame sides is useful.

The center paddle 360 may be created as a separate piece and snapped into a corresponding connector in the interior of the raised ridge 354. Alternatively, the center paddle 360 and the removable top 350 may be molded as one piece.

Addition of Minor Wall Features

Figure 19:
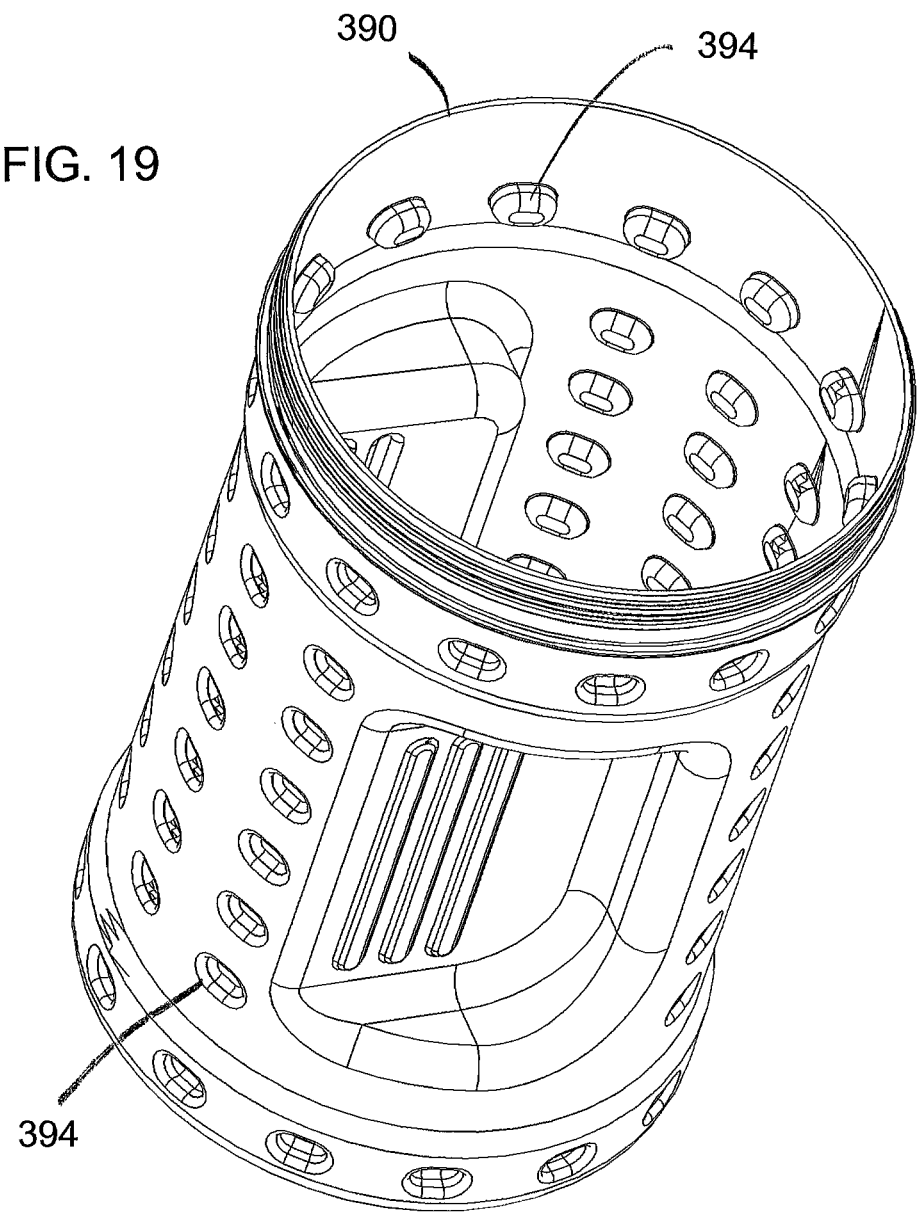
FIG. 19 illustrates a slush bottle 390 that has a series of dimples 394.

FIG. 19 illustrates a slush bottle 390 that is much like slush bottle 300 but has the addition of a series of dimples 394. A range of different dimple shapes and dimple array patterns could be used but the dimple should be convex as viewed from the interior of the slush bottle so that the dimple provides additional agitation to prevent localized areas of stagnant fluid. Since all cooling occurs through the bottle walls, if there are any stagnant or low circulation regions along the walls, those areas will freeze first. The minor wall feature geometries will likely be small dimples as shown here, ribs, or analogous structures; basically anything that can cause a disruption to the boundary layer of fluid next to the wall. A concave dimple (as viewed from the interior of the slush bottle 390) would be prone to having ice form and collect in the cavity of the dimple.

Alternative Way of Rotating the Slush Bottle

Figure 20:
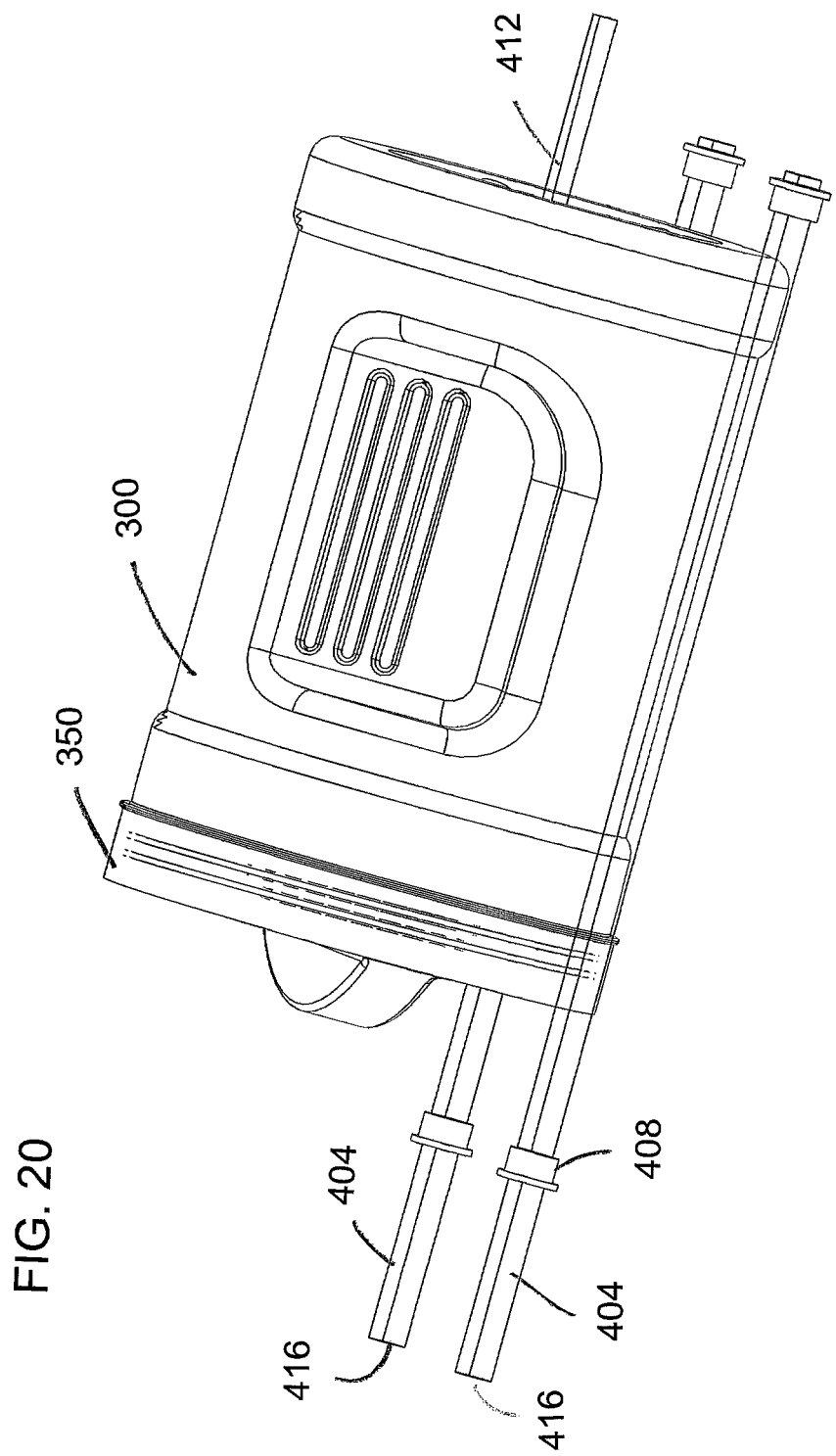
FIG. 20 shows only a few components from a device for the production of surgical slush to emphasize the use of a pair of rollers 404.

FIG. 20 shows only a few components from a device for the production of surgical slush. The other components have been rendered invisible to isolate the components relevant to this teaching.

The disclosure set forth above shows how to rotate a slush bottle by placing the slush bottle into a slush bottle carriage and then rotating the slush bottle carriage and thus the slush bottle. An alternative is to place the slush bottle between two rollers and then rotate one or more of the rollers to cause the slush bottle to rotate.

FIG. 20 shows slush bottle 300 with removable top 350. A pair of rollers 404 (shown here as transparent to allow the bottle to be seen) and a centerline probe 412 holds the slush bottle 300 with removable top 350 in position as the pair of rollers 404 is inclined with respect to horizontal.

The angle of the centerline of the slush bottle relative to horizontal may be 20 or 30 degrees which balances the desire to have gravity maintain contact of the bottle bottom with the centerline probe 412 while avoiding problems in having the rollers 404 roll the slush bottle 300 which becomes more difficult as the deviation from horizontal becomes more severe.

A tilted slush bottle will tend to keep slush at the centerline to provide a temperature indication of the slush to the centerline probe better than a horizontal orientation as a tilted orientation will shift slush toward the centerline when the slush bottle is less than half filled with saline and slush.

The use of a threaded engagement between the slush bottle 300 and the removable top 350 allows for a water tight seal of the slush bottle 300.

Centerline probe 412 monitors the temperature of the exterior of the slush bottle 300 for use with a control system for the device for making slush. Placing the probe at the centerline of rotation of the slush bottle 300 allows for consistent monitoring of one place on the slush bottle 300 rather than a ring of locations. The temperature probe used with the centerline probe 412 is apt to be a metal like stainless steel and thus not likely to wear from contact with the plastic bottle. Spinning the bottom exterior of the slush bottle 300 against the temperature probe helps maintain intimate contact by avoiding ice buildup between the bottom of the slush bottle and the centerline probe 412. Those of skill in the art can choose a temperature monitoring device such as a thermocouple, thermistor, RTD (Resistance Temperature Detection), or other appropriate device.

A set of four bushings 408 is shown to indicate that in this embodiment the rollers 404 pass through the walls in the chilled area. The drive mechanism for rotating one or both of the pairs of rollers 404 can be any suitable drive mechanism. The drive mechanism may be connected to the end 416 of one or both rollers 404. Driving both rollers 404 may be more reliable as there may be a build-up of frost on the bottle exterior which may cause slippage and using the slush bottle 300 to cause the non-driven roller to rotate adds resistance that the one driven roller must overcome. A simple motor driven belt turning pulleys on the end of each of the two rollers 404 for a given slush bottle 300 is one solution. Those of skill in the art can implement many different arrangements for driving the rollers 404.

While the rollers 404 may be driven in one direction at a fixed speed other non-uniform patterns may be advantageous. One option is to repeatedly follow a cycle of A) driving the rollers 404 clockwise for a period of time; B) ceasing driving the rollers 404; C) driving the rollers 404 counter-clockwise for a period of time; and D) ceasing driving counter-clockwise. Another option is to always drive the rollers 404 in the same direction but periodically alter the speed of rotation.

Figure 21:
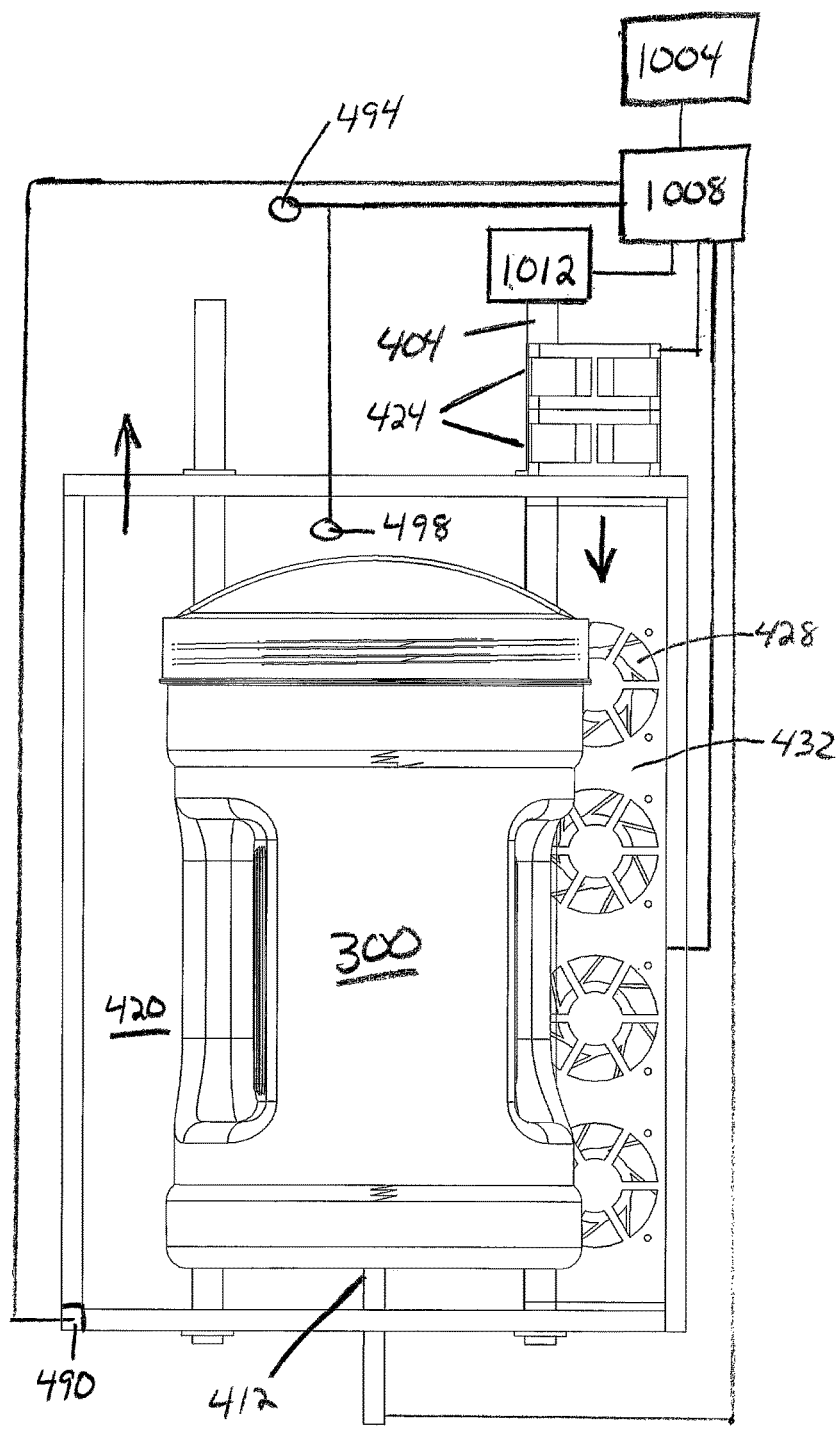
FIG. 21 shows a high level description of the control system.

FIG. 21 shows a high level description of the control system. Control system 1008 controls the overall cooling of the device interior via cooling system 1004. Control system 1008 works with the cooling unit 1004 to cool a sink chamber of chilled air adjacent to the compartment 420 to a temperature well below what is needed for use in compartment 420. The control system uses sink chamber temperature sensor 494. This chamber may be augmented with a metal block or analogous item to add thermal mass so that the reservoir of chilled air is more than sufficient to continue to act as a heat sink even as the refrigeration equipment (not shown here) goes through a normal defrost cycle and stops providing cooling temporarily. Thus, the temperature for the chamber air may be targeted to negative 25 degrees Fahrenheit though the temperature used for sustained chilling of the slush bottle 300 may be in the range of negative 8 degrees Fahrenheit.

Control system 1008 is in communication with centerline probe 412 and optionally one or more compartment temperature sensors 498 for compartment 420 (shown here with compartment lid removed). Control system 1008 controls drive system 1012 which may drive both rather than just one roller 404. Above the right roller 404 is a series of one or more drive fans 424 which drive cold air into compartment 420. Air exits the compartment via vents 436 (see FIG. 23) to the left of the left roller.

Continuing with FIG. 21, a number of circulation fans 428 suspended above the floor of the compartment 420 by fan bracket 432 are controlled by the control system 1008. When door open indicator 490 indicates that the lid covering the compartment 420 has been lifted, the control system 1008 may turn off the drive fan 424 to avoid sending more cold air to an open compartment and turn off circulation fans 428 so that the cold air in the compartment 420 settles downward to be largely retained by the compartments vertical walls.

The control system 1008 may monitor the compartment 420 air temperature and the bottle surface temperature to get an indication of the liquid/slush temperature. As the reading from the centerline probe 412 will be impacted by both the temperature of the slush bottle bottom and the temperature of the compartment air, the estimated temperature of the slush bottle interior is a function of the temperature readings at 412 and 498. The control system can respond to a relatively high temperature estimate for the slush bottle interior to aggressively drop the air temperature in the compartment 420 around the slush bottle 300 to accelerate cooling to near the temperature for freezing the saline and then allow the temperature to rise to closer to the freezing temperature. Thus, the compartment may be aggressively chilled then allowed to rise to approximately negative 8 degrees Fahrenheit.

Slush Station

Figure 22:
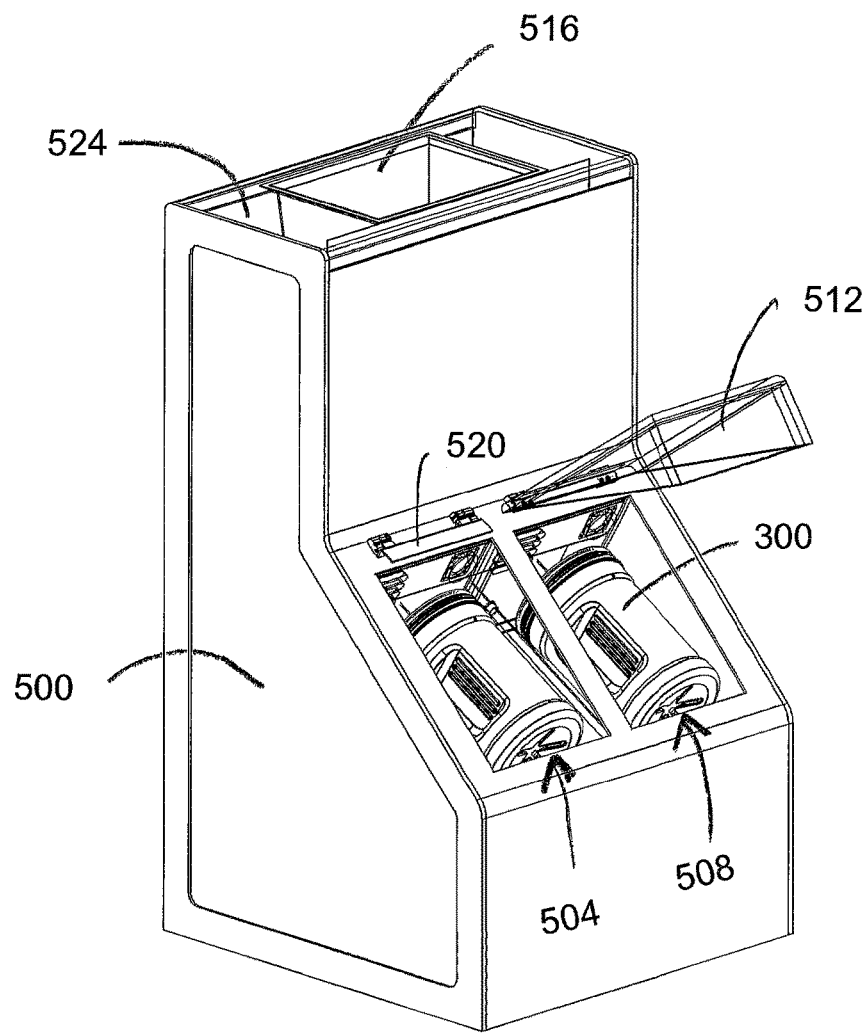
FIG. 22 shows a perspective view of the left side, front, and top of a slush station 500.

FIG. 22 shows a perspective view of the left side, front, and top of a slush station 500. This slush station has two slush making compartments 504 and 508. Each slush making compartment has a compartment lid 512. Preferably, the lid is at least partially translucent so a user can see whether the compartment has a slush bottle 300. The compartment lid for slush compartment 504 is omitted here so that lid hinge 520 and other components can be seen without distraction from the edges of the compartment lid.

Use of a compartment lid 512 so that the slush bottle 300 is totally enclosed reduces the amount of condensation to be handled by the cooling system and reduces the ingress of heat from ambient air.

On top of the slush station 500 is a basin shell 516 that may receive a slush basin for holding surgical slush being used by the operating room personnel. (The top cover 524 of the slush station is shown as transparent to help show detail.) A drape may be placed to surround the metal basin shell 516 to isolate the upper part of the slush station from the sterile field. The lower part of the slush station would not be part of the sterile field although the interior of the slush bottle 300 would be maintained as sterile. Alternatively, a drape that is fitted to the shape of the basin shell 516 may be placed over the slush station 500 including the basin shell 516. As the basin shell 516 acts as a heat sink for a corresponding inserted basin (not shown), a conforming fit for the drape, basin shell 516, and basin is desirable.

Figure 23:
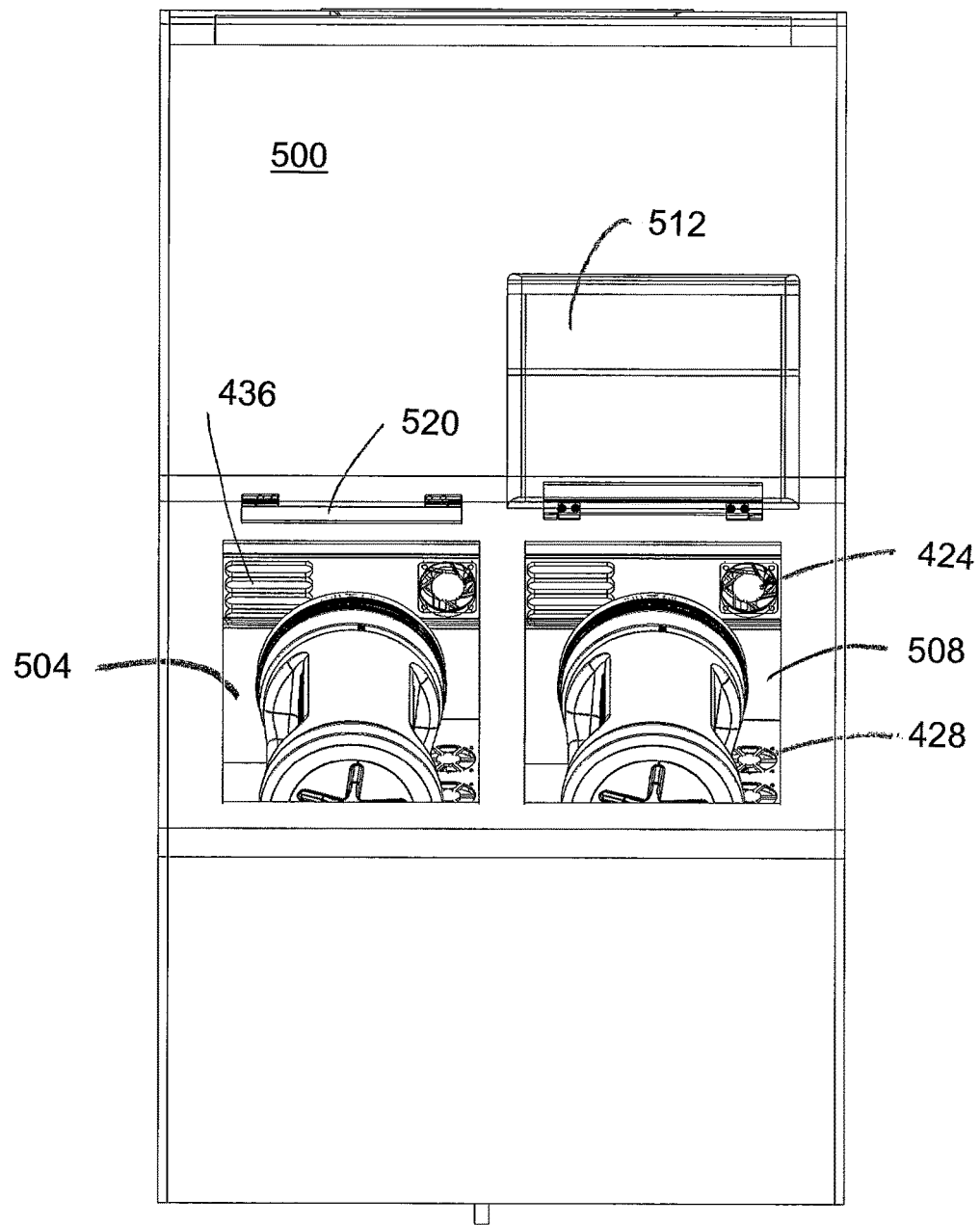
FIG. 23 shows a front view of slush station 500 with the compartment lid for compartment 504 removed.

FIG. 23 shows a front view of slush station 500 with the compartment lid for compartment 504 removed. Visible in this view are compartment lid 512, compartments 504 and 508, circulations fans 428, drive fans 424, and air vents 436.

Figure 24:
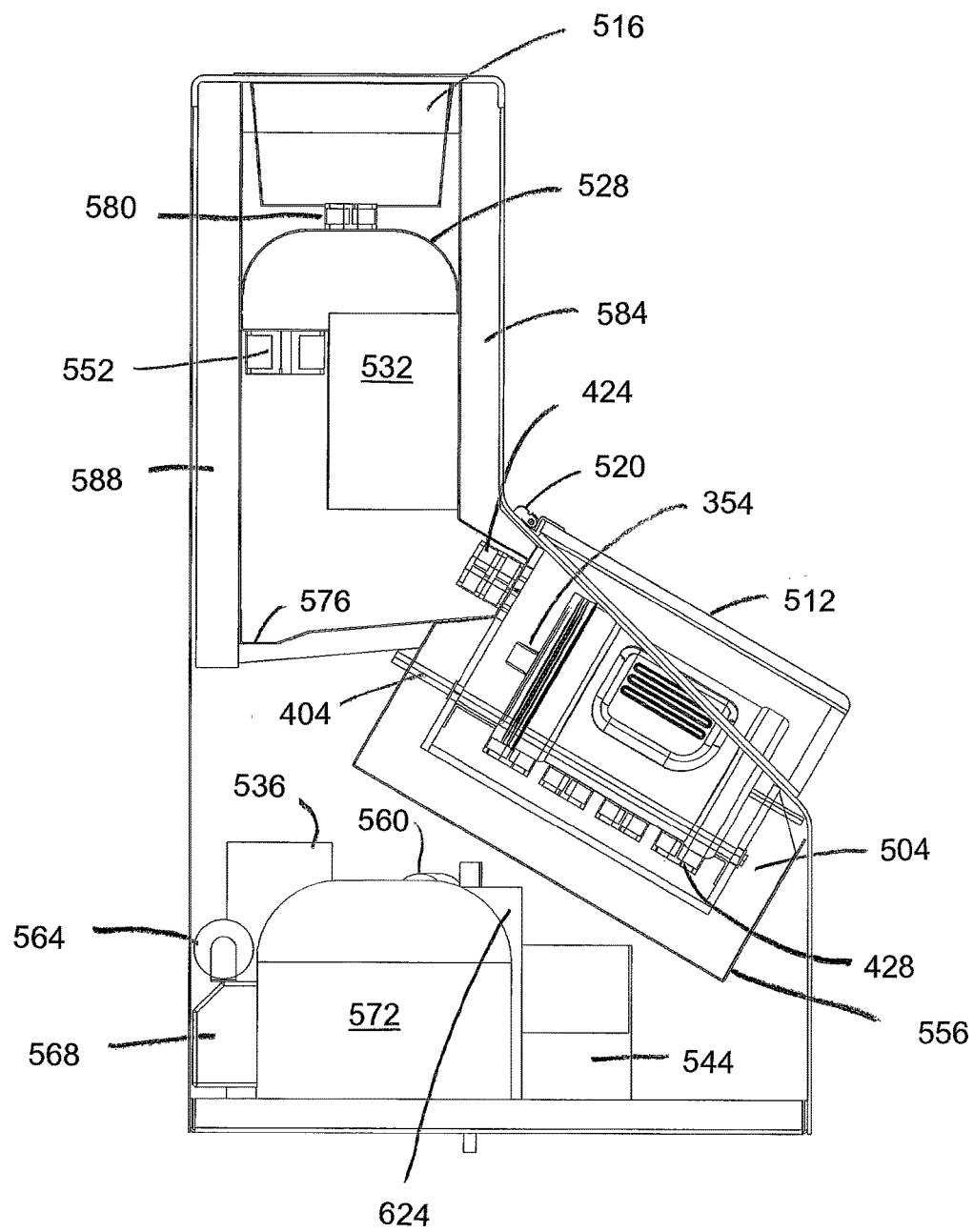
FIG. 24 is a left side view of the slush station 500 with a number of components made invisible to allow a view of interior components.

FIG. 24 is a left side view of the slush station 500 with a number of components made invisible to allow a view of interior components. Wiring connections and various components to capture and channel condensation, and other miscellaneous conventional items not needed to convey the teachings of this disclosure are not shown. These views to show internal components provide an example of how the major components might be placed in the housing.

From this view, one can see basin shell 516, sink chamber top 528, fan 552, evaporator 532, hinge 520, raised ridge 354 of removable top 350, compartment lid 512 for the compartment 504, roller 404 (drive mechanism not shown), drive fans 424, circulation fans 428, bottle insulator shield 556, condenser 536, refrigerant filter 560, compressor pressure switch 544, compressor start capacitor 564, compressor control junction box 568, compressor 572, accumulator 624, and condensate collection pan 576 (made invisible in other views). Basin chamber fan 580 is actually located in the foreground relative to basin shell 516 and there is a corresponding basin chamber vent 592 (not visible here) on the opposite side of basin shell 516. While there are a number of insulated areas, in order to understand the air circulation it is useful to include front insulation 584 and rear insulation 588.

Figure 25:
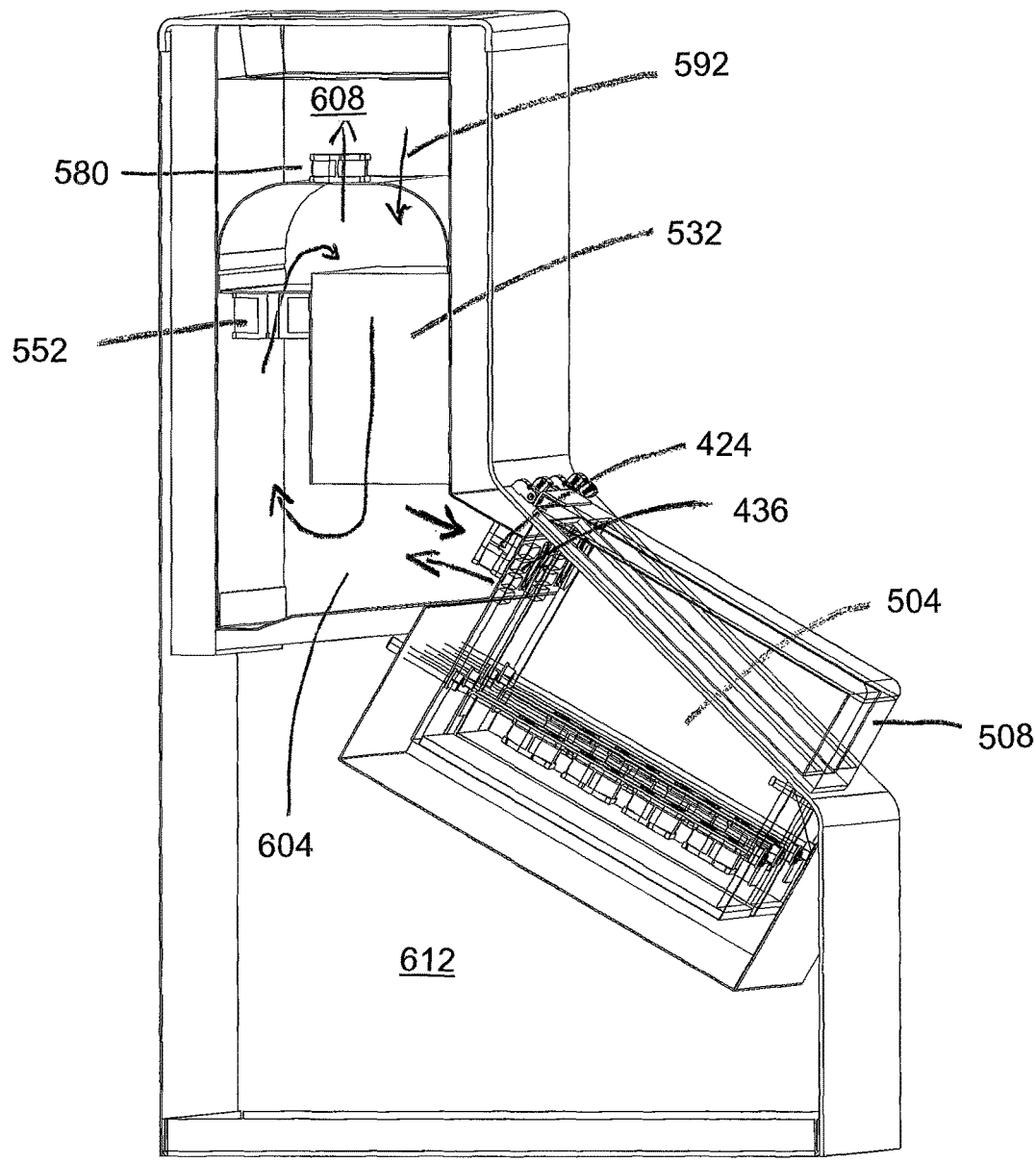
FIG. 25 was made by rotating FIG. 24 slightly and made a number of additional components invisible.

FIG. 25 was made by rotating FIG. 24 slightly and made a number of additional components invisible. FIG. 25 is useful to show the four major air chambers and their air flow patterns. The first chamber is the sink chamber 604. This chamber is chilled by the refrigeration system to provide a significant ability to act as a heat sink for other chambers even when the refrigeration equipment is not currently cooling the sink chamber 604 as the equipment is going through a defrost cycle. The sink chamber 604 may have metal or some other material added to the sink chamber 604 to increase the thermal mass of the sink chamber 604. The sink chamber 604 is chilled possibly to the range of negative 25 degrees Fahrenheit by blowing air up through fan 552 and down through the evaporator 532 which is not a box as shown here but is a heat exchanger.

The basin chamber 608 is above the sink chamber 604 and receives cold air from the sink chamber 604 via the basin chamber fan 580 which is controlled by the control system to drive the temperature of the basin chamber 608 to a desired set point to allow the thermally conductive basin shell 516 to draw heat from a slush mixture in a basin to offset the heat ingress to the slush from the ambient air of the surgical room. Driving air into the basin chamber 608 causes airflow through vent 592 as represented by the arrow. The control system may be set to maintain a temperature of about zero degrees Fahrenheit in basin chamber 608 but this number may be set to a different temperature depending on the ambient air temperature of the surgery room, and the heat transfer characteristics of the slush station 500.

Slush making compartment 504 receives chilled air from sink chamber 604 by operation of drive fans 424. The drive fans 424 are controlled by the control system to achieve a desired temperature of the air in the slush making compartment 504. Warmer air is returned through air vents 436 to the sink chamber 604.

Slush making compartment 508 is separately controlled but operates in an analogous way to slush making compartment 504.

Continuing with FIG. 25, equipment cavity 612 contains the compressor 572 and other equipment. This equipment gives off heat and thus equipment cavity 612 is separated from the adjacent sink chamber 604 and the slush making compartments 504 and 508.

Figure 26:
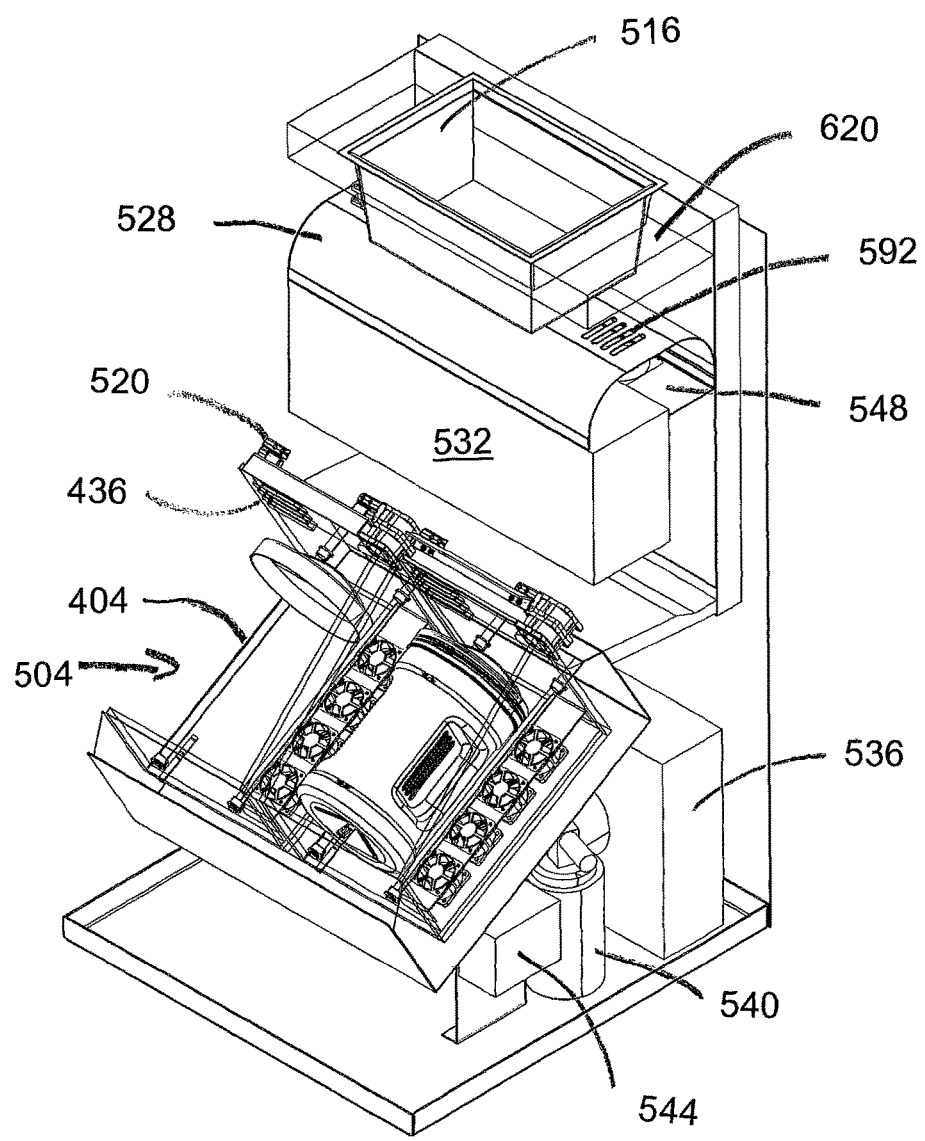
FIG. 26 is a top front right perspective view of slush station 500 with a number of components rendered invisible to allow visualization of the relative position of other components of interest.

FIG. 26 is a top front right perspective view of slush station 500 with a number of components rendered invisible to allow visualization of the relative position of other components of interest. As the slush bottle for compartment 504 has been made invisible except for removable top 350 (shown here in an embodiment without a center paddle). Vents 436, lid hinges 520, and rollers 404 are visible. Starting from the top of the slush station 500, the visible components are the basin shell 516, top insulation 620, sink chamber top 528, basin chamber vent 592, evaporator air guide 548, evaporator 532 (shown as a box rather than with all the details of a heat exchanger), condenser 536, receiver 540, and compressor pressure switch 544. The basin shell 516 is made of metal or some other material that has high thermal conductivity to serve as a heat sink to draw off heat from a correspondingly sized basin (possibly made of a polymer) that is placed into the basin shell 516. As noted above, slush added to the inserted basin would be maintained as slush as the chilled basin shell 516 would counteract the heat ingress to the slush from the ambient air.

Figure 27:
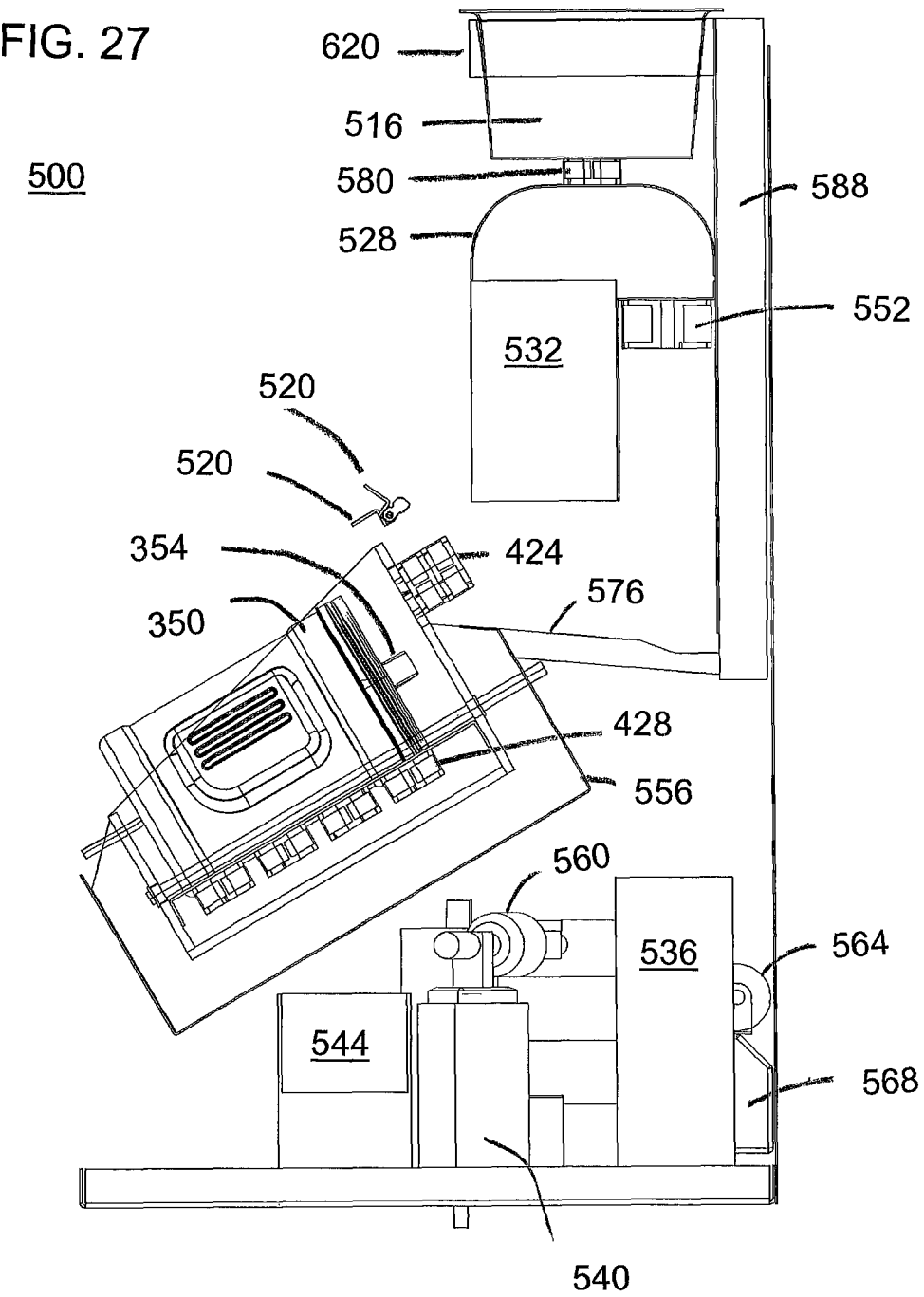
FIG. 27 shows the right side of the slush station 500 with the same components rendered invisible.

FIG. 27 shows the right side of the slush station 500 with the same components rendered invisible. From this view, one can see basin shell 516, sink chamber top 528, fan 552, evaporator 532, hinges 520 for the two compartment lids (one up and one down but both invisible), raised ridge 354 of removable top 350, roller 404 (drive mechanism not shown), drive fans 424, circulation fans 428, bottle insulator shield 556, condenser 536, refrigerant filter 560, receiver 540, compressor pressure switch 544, compressor start capacitor 564, and compressor control junction box 568. Also visible are rear insulation 588, top insulation 620, and basin chamber fan 580.

Figure 28:
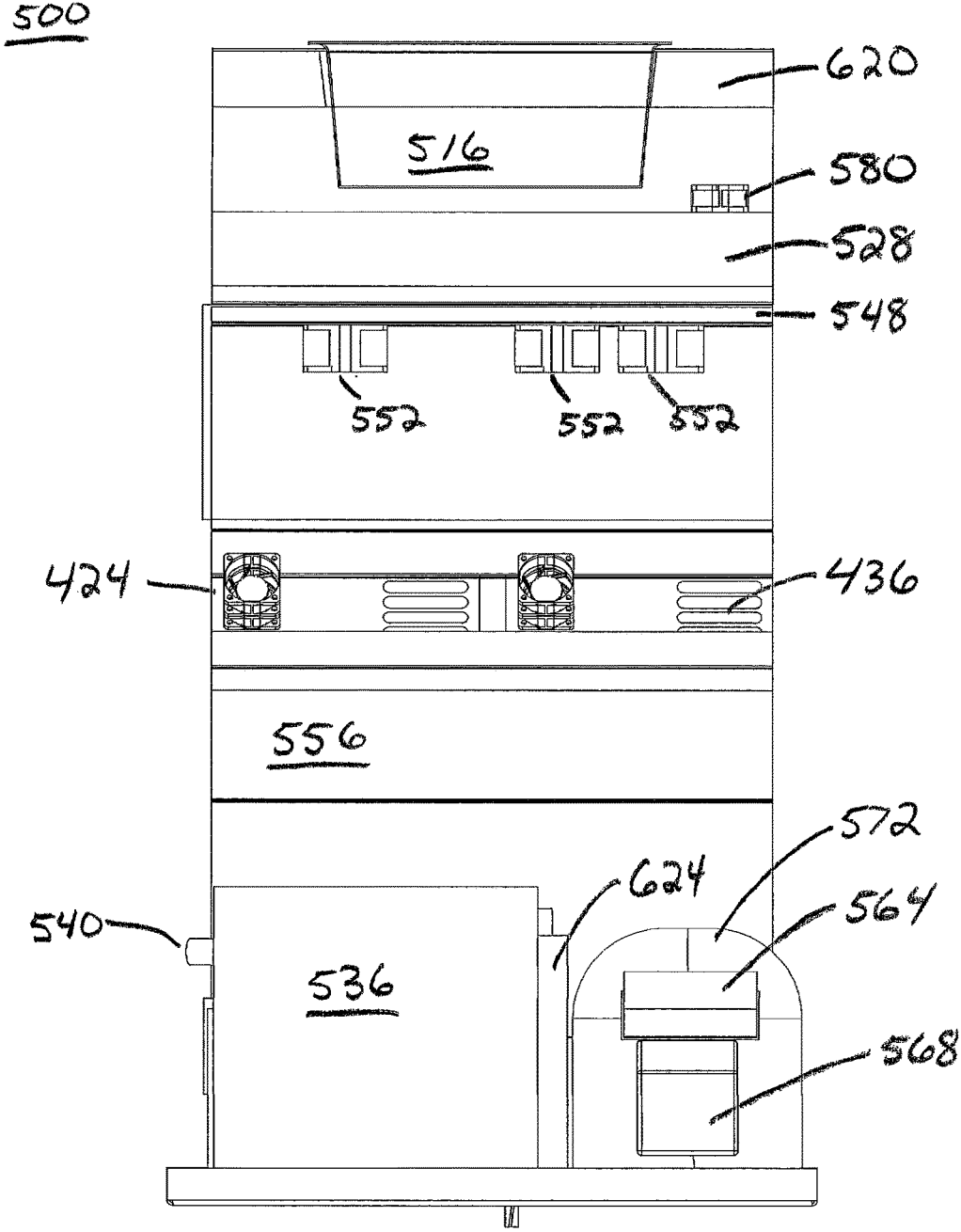
FIG. 28 shows the rear of the slush station 500 with the same components rendered invisible.

FIG. 28 shows the rear of the slush station 500 with the same components rendered invisible. From this view, one can see basin shell 516, sink chamber top 528, evaporator air guide 548, three fans 552 (not to scale), drive fans 424, air vents 436, bottle insulator shield 556, condenser 536, receiver 540, compressor start capacitor 564, compressor control junction box 568, and compressor 572. Also visible in FIG. 28 are top insulation 620 and basin chamber fan 580.

Figure 29:
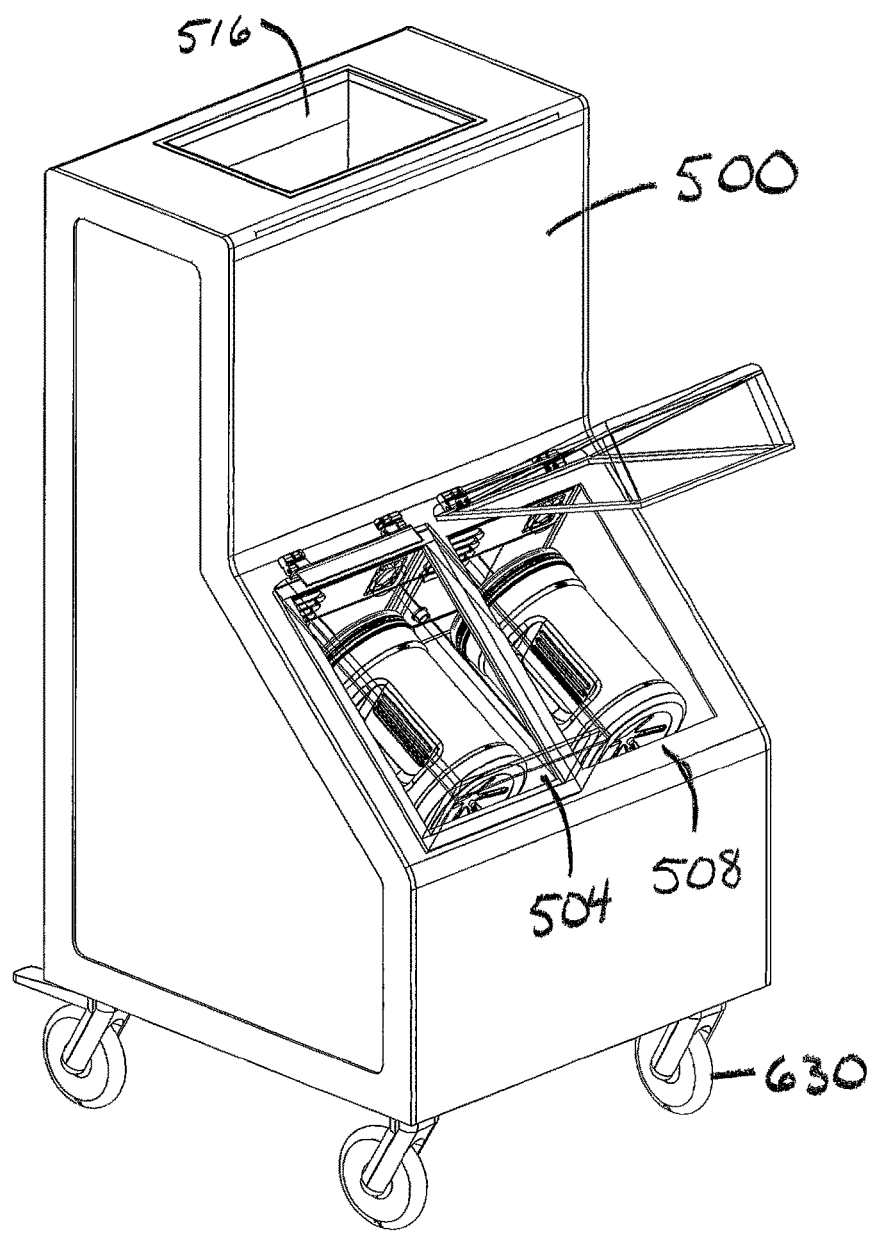
FIG. 29 is a top, right, front perspective view that shows slush station 500 with compartment 504 closed and compartment 508 open.

FIG. 29 is a top, right, front perspective view that shows slush station 500 with compartment 504 closed and compartment 508 open. FIG. 29 includes optional casters 630.

Vertical Orientation of the Slush Bottle

The disclosure set forth above notes that it is useful to orient the slush bottle in some orientation other than vertical or upside down in order to promote the lifting of slush to allow the falling of the slush to condition the slush to form atraumatic slush. The teachings of the present disclosure may be extended to include devices for the production of sterile slush if one or more of the following are adapted.

Complex Rotational Motion

Mixing could be performed by spinning the slush bottle about its axis while also orbiting the slush bottle about an axis that is not aligned with the bottle axis. This complex movement would cause slush to be pressed against a portion of the wall for a moment and then fall. Even the slush that was below the water level of the slush/saline slurry would impact the side walls to condition the slush to form atraumatic slush without large crystalline structures. One suitable device for this complex rotational motion is shown in FIG. 30.

Figure 30:
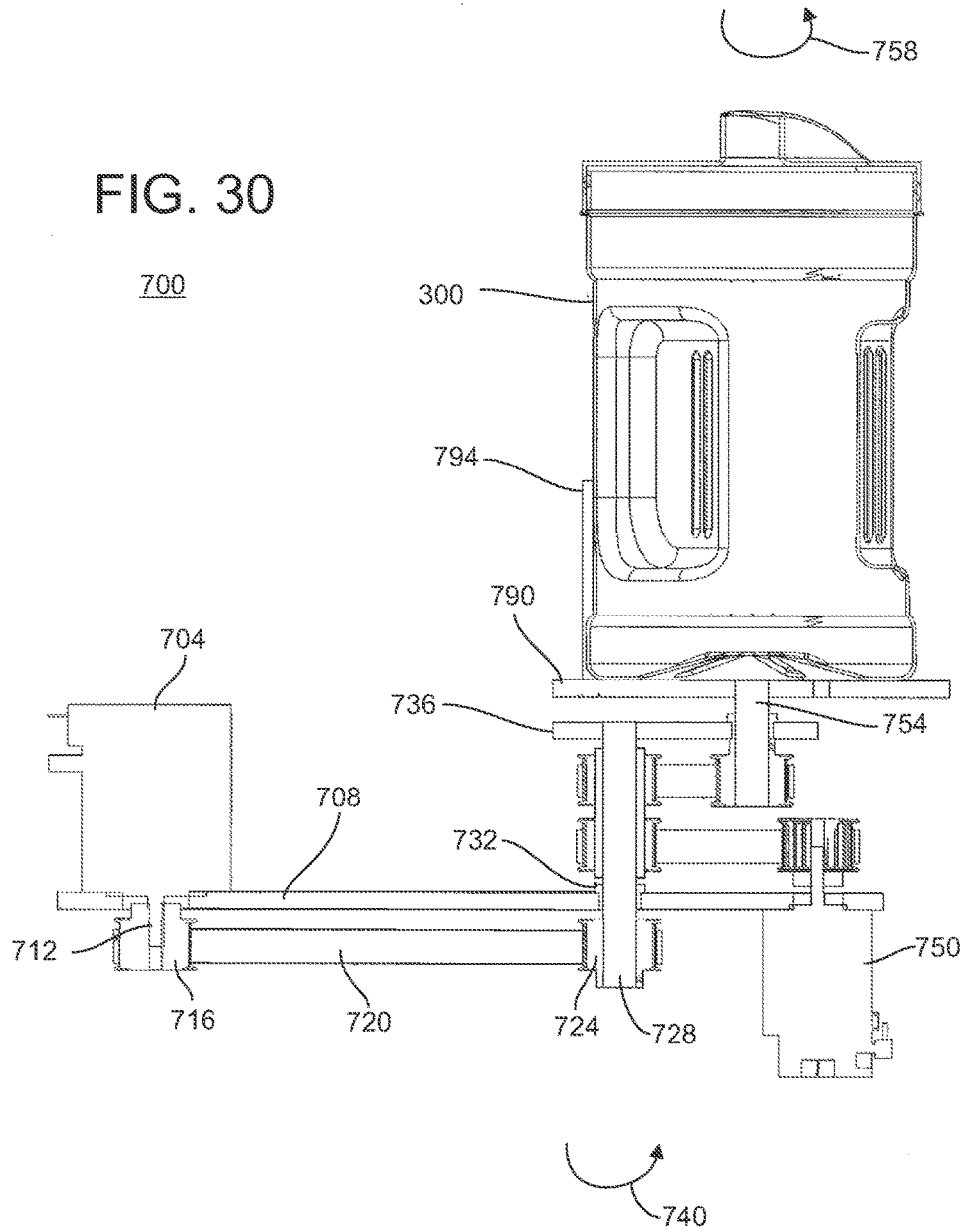
FIG. 30 is a cross section of a rotation device 700.

FIG. 30 is shown in cross section to allow the differences between bushings and sleeves to be highlighted.

Rotation device 700 has two rotating shafts: bottle shaft 754 and orbital shaft 728. The bottle shaft 754 is driven to rotate slush bottle 300 around the slush bottle's longitudinal axis as indicated by arrow 758. A second rotation 740 occurs around orbital shaft 728. The second rotation causes bottle shaft 754 to rotate around orbital shaft 728.

Orbital motor 704 mounted on plate 708 drives motor shaft 712. Motor shaft 712 drives pulley 716 which in turn drives pulley 724 by belt 720. Pulley 724 drives orbital shaft 728 which passes through plate 708 via bushing 732. Rotating orbital shaft 728 rotates upper plate 736. Ignoring for now the potential for bottle shaft 754 to rotate, the rotation of orbital shaft 728 rotates bottle shaft 754 and bottle platform 790 including retention poles 794 which hold the slush bottle 300. Compare FIG. 30 to FIG. 32 which shows bottle shaft 754 between orbital shaft 728 and orbital motor 704.

Figure 31:
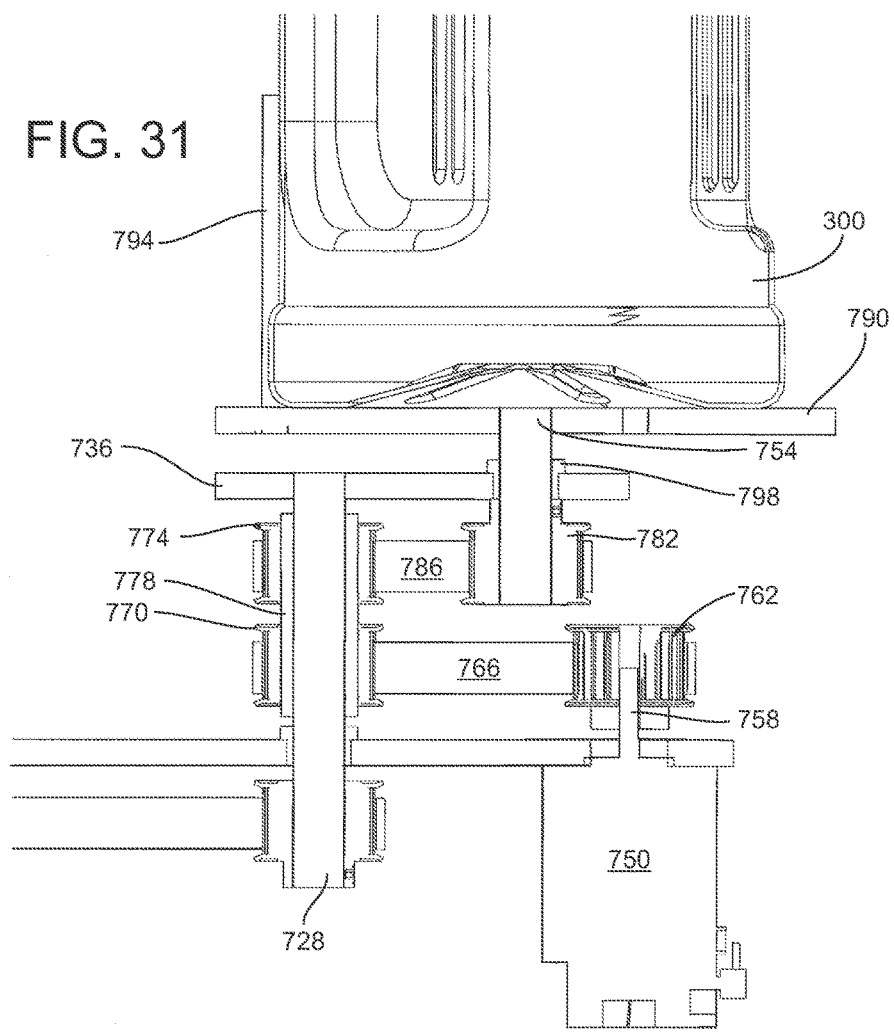
FIG. 31 is an enlarged view of a portion of FIG. 31 showing components of interest for the rotation of the bottle shaft 754.

FIG. 31 shows a segment of FIG. 30 enlarged to allow labeling of components of interest for the rotation of the bottle shaft 754. Bottle motor 750 drives motor shaft 758 which drives pulley 762. Pulley 762 drives pulley 770 via belt 766. Pulley 770 drives pulley 774 via sleeve 778. Pulley 774 drives pulley 782 via belt 786. Pulley 782 rotates bottle platform 790 around shaft 754 which passes through upper plate 736 via bushing 798.

Figure 32:
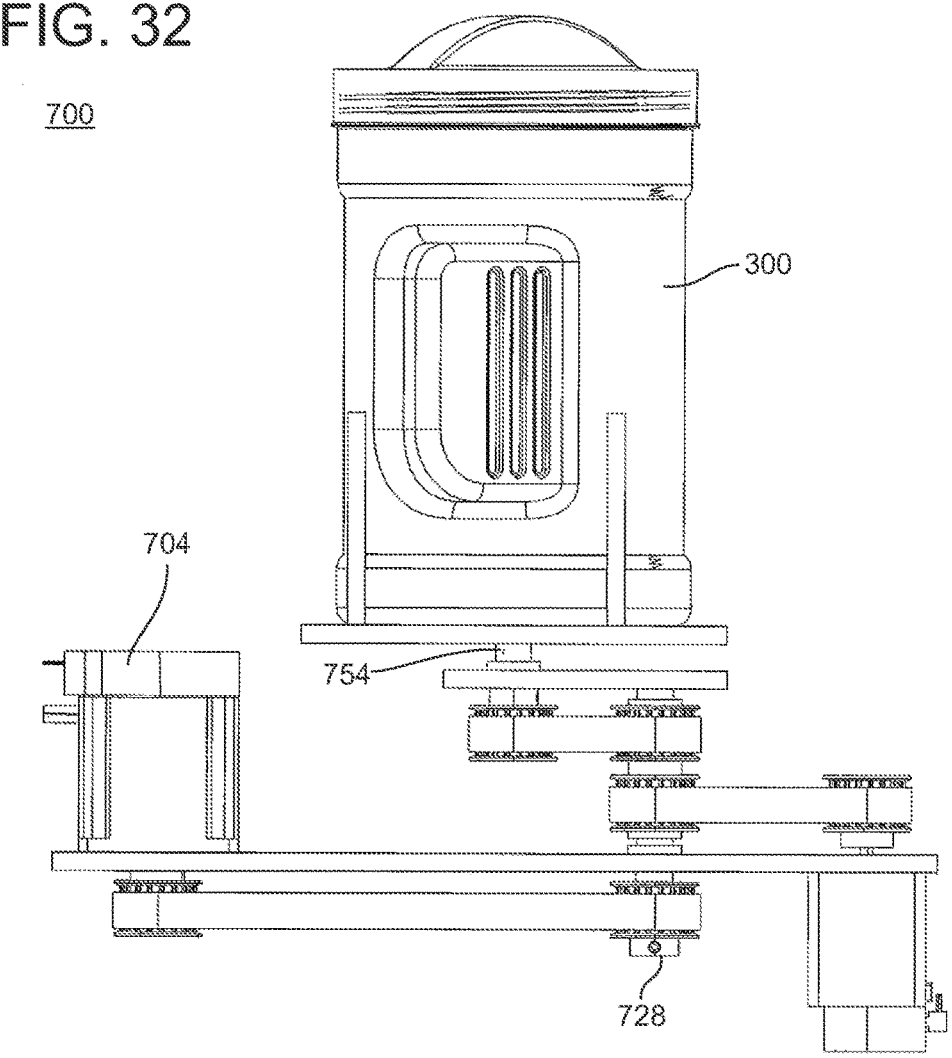
FIG. 32 is a view of rotational device 700 which has rotated relative to the position in FIG. 30.

The spinning device of FIGS. 30-32 can implement a range of complex motion for a slush bottle 300. This motion could be further complicated by moving the centerline of the slush bottle 300 away from the centerline of bottle shaft 754. Another alternative would be to adjust the spinning of the slush bottle 300 relative to the spinning around orbital shaft 728 to establish a vortex within the slurry in the slush bottle 300.

Figure 33:
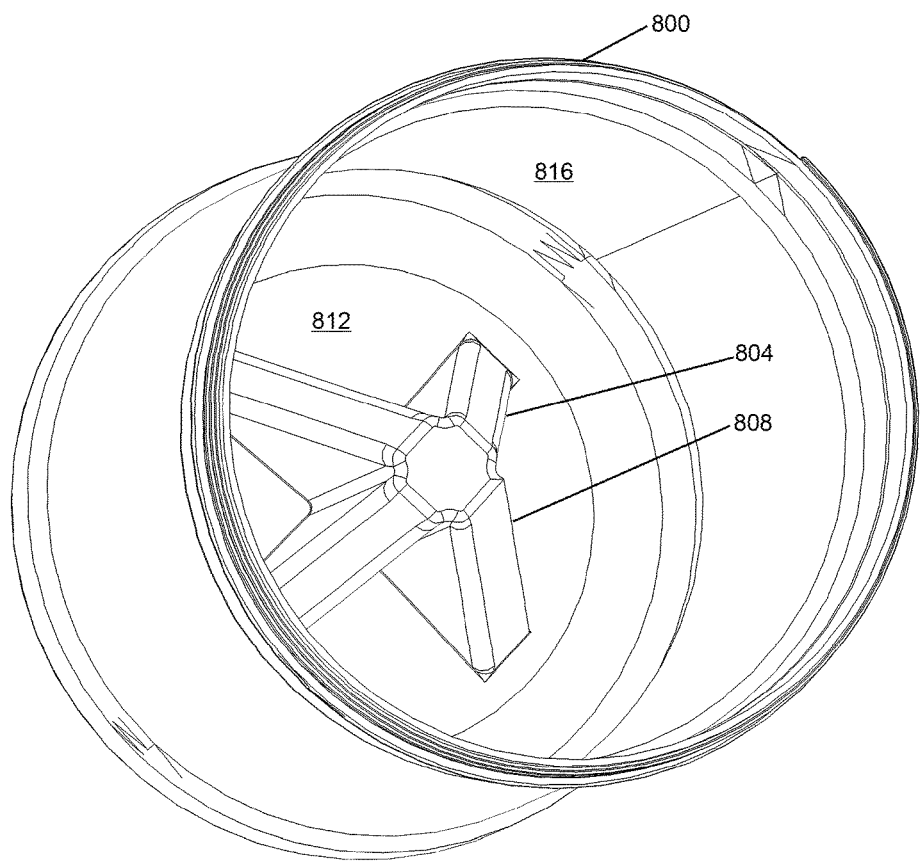
FIG. 33 is a top perspective view of slush bottle 800 with center feature 804.
Figure 34:
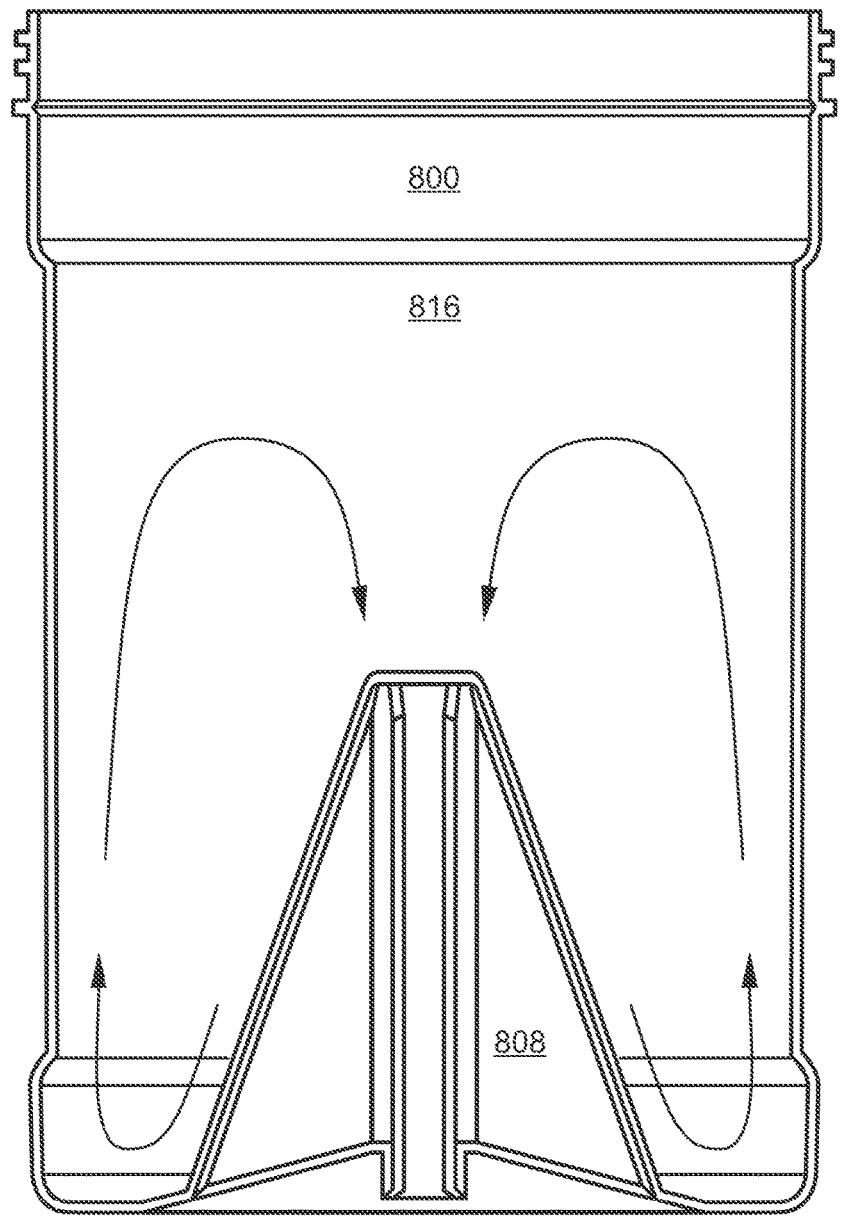
FIG. 34 is a side view of a cross section of slush bottle 800.
Figure 35:
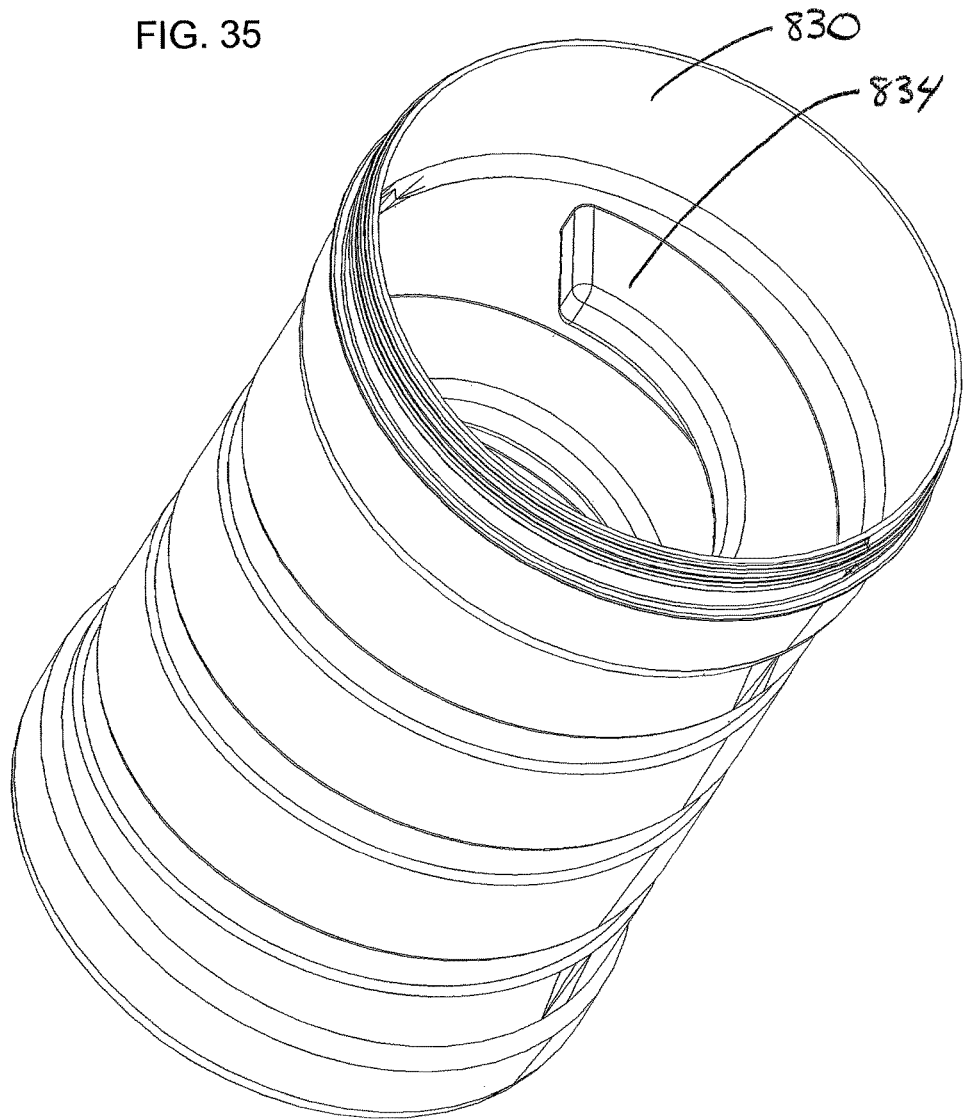
FIG. 35 is a top perspective view of slush bottle 830 with thread 834.
Figure 36:
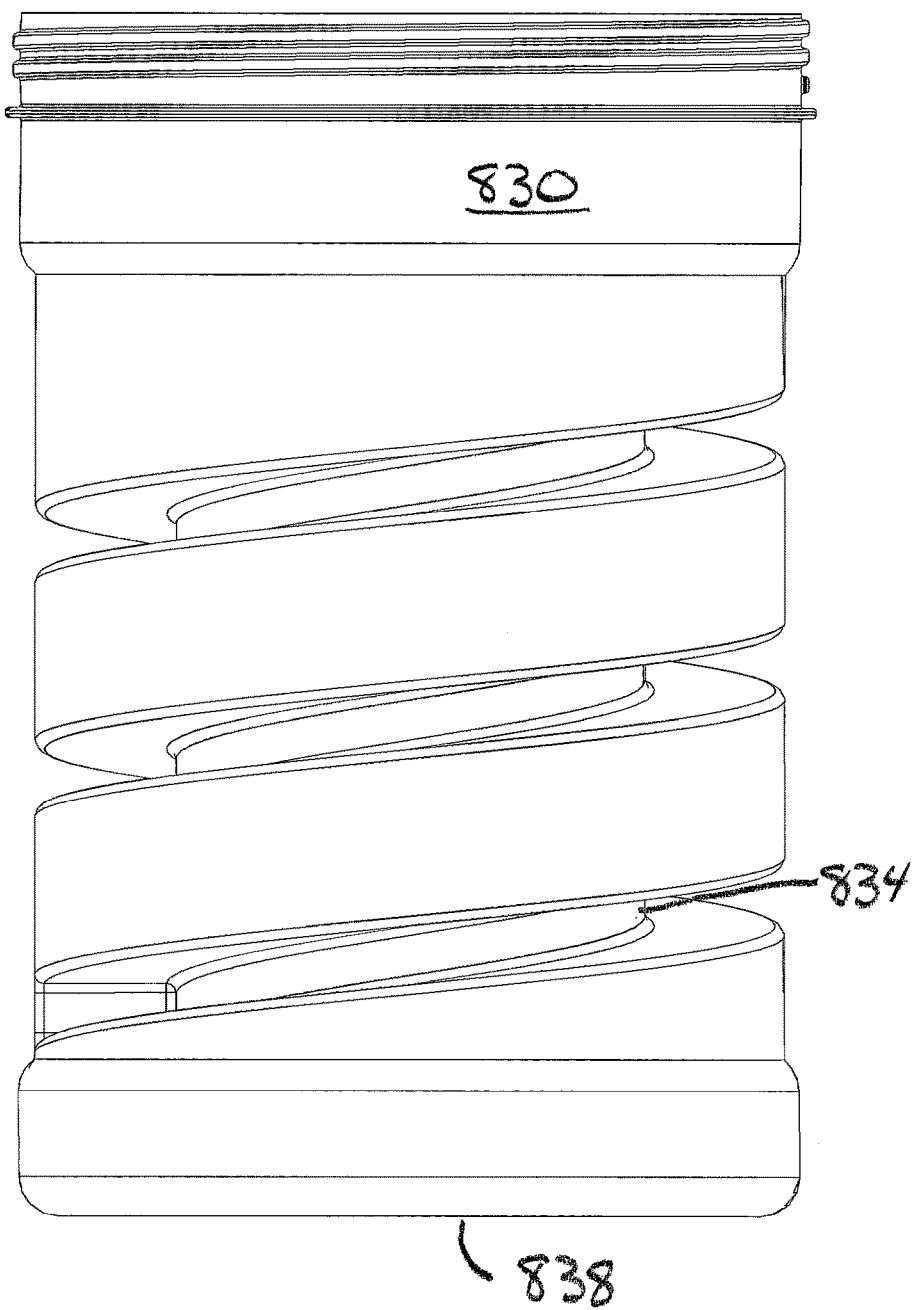
FIG. 36 is a side view of slush bottle 830.
Figure 37:
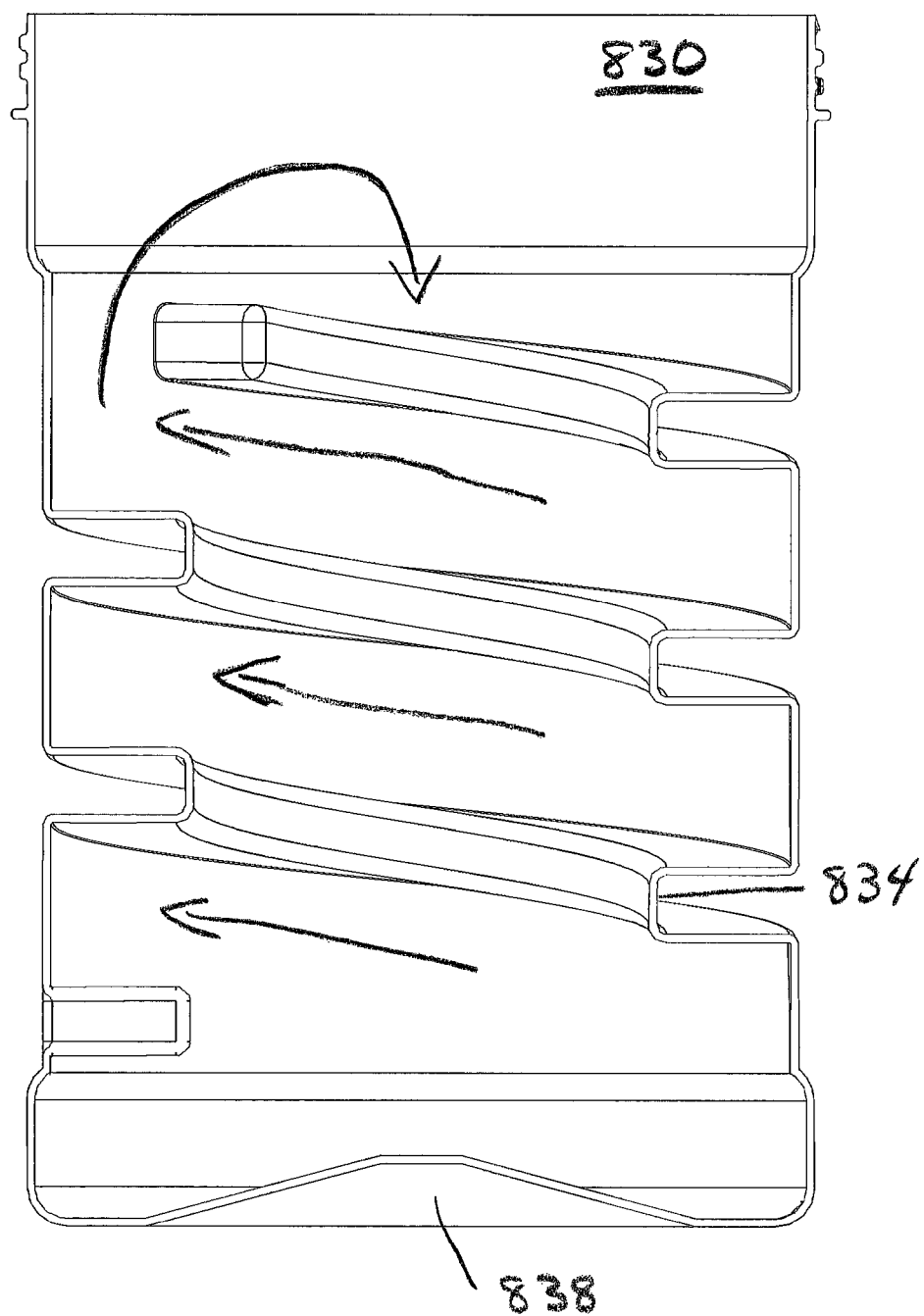
FIG. 37 is a side view of a cross section of slush bottle 830.
Figure 38:
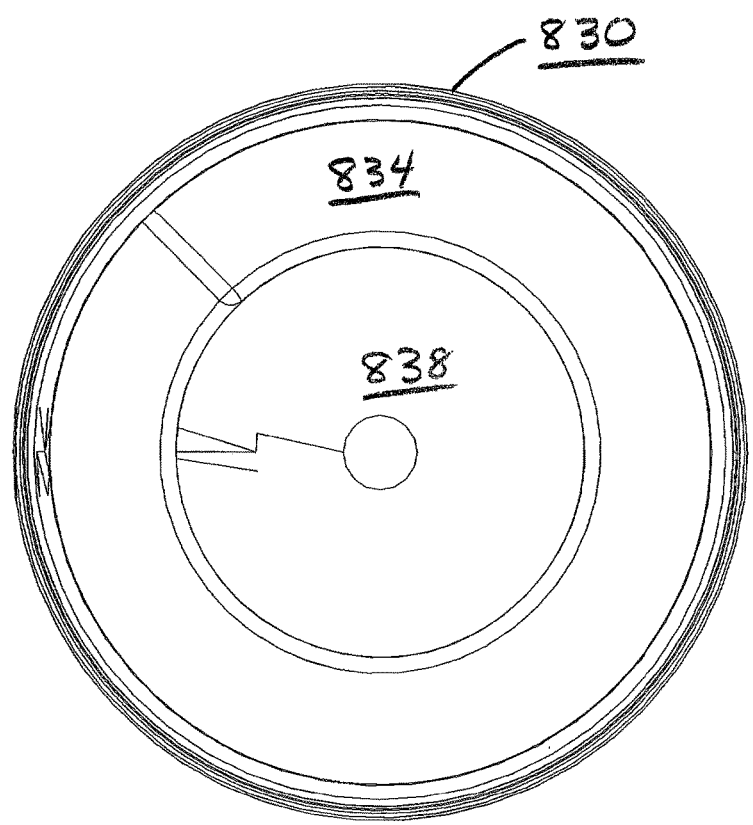
FIG. 38 is a top view of slush bottle 830.
Figure 39:
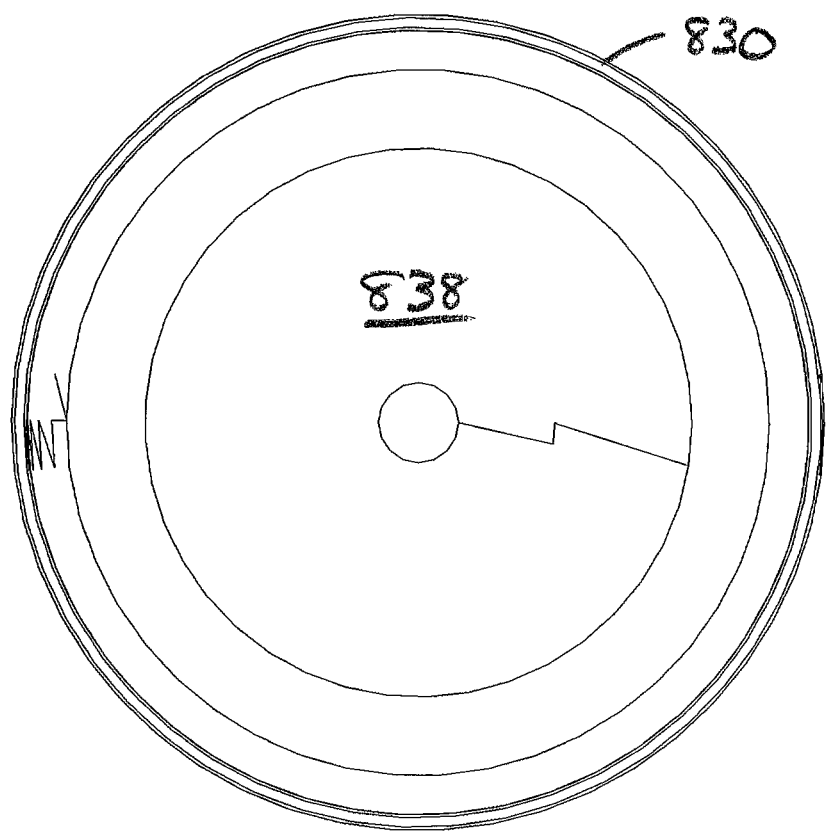
FIG. 39 is a bottom view of slush bottle 830.

FIGS. 33 and 34 show a slush bottle 800 that may be used in a vertical orientation. The slush bottle 800 has center feature 804 with a set of ribs 808. Rotating the slush bottle 800 back and forth with a rotation of about 45 to 90 degrees will tend to push slush radially outward from the lower ends of the ribs 808. The radial outward movement of slush along the bottom 812 the slush bottle 800 will tend to push slush up the outer walls 816 as shown by the arrows in the cross section view of FIG. 34. As slush is moved up the outer walls 816 it will move back to the center. This agitated slurry of migrating slush will tend to retard the growth of loose aggregation of slush into slush balls and the formation of larger crystals of ice.

A slush bottle could be implemented with a large thread structure on a central core. This slush bottle could be rotated in a clockwise direction and the screw structure would tend to move slush up the central region of the slush bottle and down the side walls to agitate and circulate the slush. Periodically the slush bottle could be moved in a counter-clockwise motion to cause the screw like effect from the central core to be reversed and thus move the slush in the opposite direction at the central core and at the side walls. The central core could extend from the slush bottle bottom, the removable top, or both. The proportion of the movement in the clockwise direction to counter-clockwise could be equal but it would not have to be.

FIGS. 35-39 show views of slush bottle 830. Slush bottle 830 has a thread 834 along the outer wall of the slush bottle 830. Rotating slush bottle 830 in one direction, even when the slush bottle 830 is in a vertical orientation will move slush toward the removable top (not shown). As slush moves up the walls toward the removable top, slush already near the top will be drawn down the centerline of the slush bottle 830 toward the bottom 838 of the slush bottle 830. Reversing the direction of rotation would reverse that pattern. Rotating an open slush bottle 830 could be used to dispense a finite amount of slush as the rotating bottle acts to advance the slush out to the removable top.

For a number of the examples given above, the movement of the slush bottle could be augmented by simultaneously or intermittently moving the slush bottle in the vertical direction to help with vertical movement of the slush relative to the bottle walls.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What is claimed is:

1. A method for making surgical slush; the method comprising:
    placing an amount of fluid within a receptacle with a bottom wall and a cylindrical vertical wall; the fluid comprising water and salt; the amount of fluid placed into the receptacle being insufficient to cover all of the cylindrical vertical wall;
    reversibly attaching the receptacle to a platform;
    rotating the platform around a first axis that runs perpendicular through the platform while
    rotating the platform around an orbital axis parallel to the first axis to impose a complex motion upon the fluid within the receptacle as there is rotation around the first axis during rotation around the orbital axis; and
    the complex motion occurring while at least a portion of the cylindrical vertical wall is exposed to air cooled below a freezing temperature for the fluid contained in the receptacle to cool the fluid to form a surgical slush.

2. The method of claim 1 wherein a removable lid is placed upon the receptacle before imposing complex motion upon the receptacle removably attached to the platform.

3. The method of claim 1 wherein the first axis is co-linear with the vertical axis of the receptacle.

4. The method of claim 1 wherein the first axis is parallel to a vertical axis of the receptacle.

5. The method of claim 1 wherein a direction of rotation of the platform around the first axis as viewed from a first vantage point is also the direction of rotation of the platform around the orbital axis.

6. The method of claim 1 wherein reversibly attaching the receptacle to a platform is accomplished by placing the receptacle in a zone defined by a set of retention poles extending from the platform.

* * * * *